United States Patent
Wallace et al.

(10) Patent No.: US 10,835,269 B1
(45) Date of Patent: Nov. 17, 2020

(54) INVERTING THROMBECTOMY APPARATUSES AND METHODS OF USE

(71) Applicant: STRYKER CORPORATION, Fremont, CA (US)

(72) Inventors: Michael P. Wallace, Pleasanton, CA (US); Clifford Van, Santa Clara, CA (US); Roy Leguidleguid, Union City, CA (US); E. Skott Greenhalgh, Gladwyne, PA (US); Winnie Tang, Pleasanton, CA (US)

(73) Assignee: Stryker Corporation, Fremont, CA (US)

( * ) Notice: Subject to any disclaimer, the term of this patent is extended or adjusted under 35 U.S.C. 154(b) by 0 days.

(21) Appl. No.: 16/594,256

(22) Filed: Oct. 7, 2019

Related U.S. Application Data

(63) Continuation of application No. PCT/US2019/050467, filed on Sep. 10, 2019.
(Continued)

(51) Int. Cl.
   *A61B 17/22* (2006.01)
   *A61B 17/3207* (2006.01)
   (Continued)

(52) U.S. Cl.
   CPC .. *A61B 17/22031* (2013.01); *A61B 17/32075* (2013.01); *A61M 25/0043* (2013.01);
   (Continued)

(58) Field of Classification Search
   CPC .... A61B 2017/22034; A61B 17/22032; A61B 17/22; A61B 17/221; A61B 2017/22035; A61B 2017/22037; A61B 2017/2215; A61B 2017/2217; A61B 2017/2212; A61B 2017/3435; A61B 17/22031; A61B 2017/22079; A61B 1/00151; A61M 25/0074; A61M 25/0043; A61M 25/0119; A61F 2/01; A61F 2/013; A61F 2/011
   (Continued)

(56) References Cited

U.S. PATENT DOCUMENTS 4,222,380 A   9/1980 Terayama
4,243,040 A   1/1981 Beecher
(Continued)

FOREIGN PATENT DOCUMENTS

AU   2015210338   8/2015
GB   1588072      4/1981
(Continued)

OTHER PUBLICATIONS

Non-Final Office Action for U.S. Appl. No. 15/496,570, dated Aug. 9, 2017.
(Continued)

*Primary Examiner* — Katherine H Schwiker
(74) *Attorney, Agent, or Firm* — Vista IP Law Group, LLP

(57) ABSTRACT

Described herein are mechanical inverting tube apparatuses that may be used to remove clot (e.g., thrombectomy), the apparatuses including an inversion support catheter having an expandable funnel-shaped distal end, and a flexible tube that can be continuously rolled over the funnel-shaped distal end and invert into the inner lumen of the inversion support catheter.

19 Claims, 27 Drawing Sheets

Related U.S. Application Data

(60) Provisional application No. 62/729,276, filed on Sep. 10, 2018.

(51) Int. Cl.
*A61M 25/06* (2006.01)
*A61M 25/00* (2006.01)

(52) U.S. Cl.
CPC .... *A61M 25/0074* (2013.01); *A61M 25/0082* (2013.01); *A61M 25/0662* (2013.01)

(58) Field of Classification Search
USPC .......................................................... 606/200
See application file for complete search history.

(56) References Cited

U.S. PATENT DOCUMENTS

| | | | |
|---|---|---|---|
| 4,324,262 A | 4/1982 | Hall | |
| 4,469,100 A | 9/1984 | Hardwick | |
| 4,604,094 A | 8/1986 | Shook | |
| 4,646,736 A | 3/1987 | Auth | |
| 4,863,440 A | 9/1989 | Chin | |
| 4,946,440 A | 8/1990 | Hall | |
| 5,329,923 A | 7/1994 | Lundquist | |
| 5,364,345 A | 11/1994 | Lowery et al. | |
| 5,389,100 A | 2/1995 | Bacich et al. | |
| 5,662,703 A | 9/1997 | Yurek et al. | |
| 5,971,938 A | 10/1999 | Hart et al. | |
| 6,156,055 A * | 12/2000 | Ravenscroft | A61B 17/221 |
| | | | 606/206 |
| 6,221,006 B1 | 4/2001 | Dubrul et al. | |
| 6,238,412 B1 | 5/2001 | Dubrul et al. | |
| 6,245,078 B1 | 6/2001 | Ouchi | |
| 6,258,115 B1 | 7/2001 | Dubrul | |
| 6,544,278 B1 | 4/2003 | Vrba et al. | |
| 6,569,181 B1 | 5/2003 | Burns | |
| 6,620,179 B2 | 9/2003 | Brook et al. | |
| 6,635,068 B1 | 10/2003 | Dubrul et al. | |
| 6,635,070 B2 | 10/2003 | Leeflang et al. | |
| 6,830,561 B2 | 12/2004 | Jansen et al. | |
| 6,846,029 B1 | 1/2005 | Ragner et al. | |
| 6,942,682 B2 | 9/2005 | Vrba et al. | |
| 7,621,870 B2 | 11/2009 | Berrada et al. | |
| 7,780,696 B2 | 8/2010 | Daniel et al. | |
| 8,057,496 B2 | 11/2011 | Fischer, Jr. | |
| 8,070,769 B2 | 12/2011 | Broome | |
| 8,092,486 B2 | 1/2012 | Berrada et al. | |
| 8,657,867 B2 | 2/2014 | Dorn et al. | |
| 8,721,714 B2 | 5/2014 | Kelley | |
| 8,784,442 B2 | 7/2014 | Jones et al. | |
| 8,795,305 B2 | 8/2014 | Martin et al. | |
| 8,956,384 B2 | 2/2015 | Berrada et al. | |
| 9,028,401 B1 | 5/2015 | Bacich et al. | |
| 9,125,683 B2 | 9/2015 | Farhangnia et al. | |
| 9,126,016 B2 | 9/2015 | Fulton | |
| 9,155,552 B2 | 10/2015 | Ulm, III | |
| 9,173,668 B2 | 11/2015 | Ulm, III | |
| 9,186,487 B2 | 11/2015 | Dubrul et al. | |
| 9,358,037 B2 | 1/2016 | Farhangnia et al. | |
| 9,259,237 B2 | 2/2016 | Quick et al. | |
| 9,351,747 B2 | 5/2016 | Kugler et al. | |
| 9,463,035 B1 | 10/2016 | Greenhalgh et al. | |
| 9,717,514 B2 | 8/2017 | Martin et al. | |
| 9,848,975 B2 | 12/2017 | Hauser | |
| 9,849,014 B2 | 12/2017 | Kusleika | |
| 9,962,178 B2 | 5/2018 | Greenhalgh et al. | |
| 10,010,335 B2 | 7/2018 | Greenhalgh et al. | |
| 10,016,266 B2 | 7/2018 | Hauser | |
| 10,028,759 B2 | 7/2018 | Wallace et al. | |
| 10,130,385 B2 | 11/2018 | Farhangnia et al. | |
| 10,271,864 B2 | 4/2019 | Greenhalgh et al. | |
| 10,327,883 B2 | 6/2019 | Yachia | |
| 2002/0032455 A1 | 3/2002 | Boock et al. | |
| 2002/0173819 A1 | 11/2002 | Leeflang et al. | |
| 2003/0083693 A1 | 5/2003 | Daniel et al. | |
| 2003/0135258 A1 | 7/2003 | Andreas et al. | |
| 2003/0153873 A1 | 8/2003 | Luther et al. | |
| 2003/0176884 A1 | 9/2003 | Berrada et al. | |
| 2003/0208224 A1 | 11/2003 | Broome | |
| 2004/0098033 A1 | 5/2004 | Leeflang et al. | |
| 2005/0085826 A1 | 4/2005 | Nair et al. | |
| 2005/0085849 A1 | 4/2005 | Sepetka et al. | |
| 2005/0119668 A1 | 6/2005 | Teague et al. | |
| 2005/0177132 A1 | 8/2005 | Lentz et al. | |
| 2005/0187570 A1 | 8/2005 | Nguyen et al. | |
| 2005/0283166 A1 | 12/2005 | Greenhalgh | |
| 2005/0283186 A1 | 12/2005 | Berrada et al. | |
| 2006/0042786 A1 | 3/2006 | West | |
| 2006/0089533 A1 | 4/2006 | Ziegler et al. | |
| 2006/0173525 A1 | 8/2006 | Behl et al. | |
| 2006/0195137 A1 | 8/2006 | Sepetka et al. | |
| 2006/0200221 A1 | 9/2006 | Malewicz | |
| 2006/0276874 A1 | 12/2006 | Wilson et al. | |
| 2006/0293696 A1 | 12/2006 | Fahey et al. | |
| 2007/0112374 A1 | 5/2007 | Paul, Jr. et al. | |
| 2007/0149996 A1 | 6/2007 | Coughlin | |
| 2007/0213765 A1 | 9/2007 | Adams et al. | |
| 2008/0183136 A1 | 7/2008 | Lenker et al. | |
| 2010/0030256 A1 | 2/2010 | Dubrul et al. | |
| 2010/0042136 A1 | 2/2010 | Berrada et al. | |
| 2010/0087844 A1 | 4/2010 | Fischer, Jr. | |
| 2010/0137846 A1 | 6/2010 | Desai et al. | |
| 2010/0190156 A1 | 7/2010 | Van Wordragen et al. | |
| 2010/0249815 A1 | 9/2010 | Jantzen et al. | |
| 2011/0034987 A1 | 2/2011 | Kennedy | |
| 2011/0118817 A1 | 5/2011 | Gunderson et al. | |
| 2011/0160763 A1 | 6/2011 | Ferrera et al. | |
| 2011/0265681 A1 | 11/2011 | Allen et al. | |
| 2011/0288529 A1 | 11/2011 | Fulton | |
| 2011/0288572 A1 | 11/2011 | Martin | |
| 2012/0083824 A1 | 4/2012 | Berrada et al. | |
| 2012/0083868 A1 | 4/2012 | Shrivastava | |
| 2012/0271105 A1 | 10/2012 | Nakamura et al. | |
| 2013/0046332 A1 | 2/2013 | Jones et al. | |
| 2013/0096571 A1 | 4/2013 | Massicotte et al. | |
| 2013/0116721 A1 | 5/2013 | Takagi et al. | |
| 2013/0226196 A1 | 8/2013 | Smith | |
| 2013/0317589 A1 | 11/2013 | Martin et al. | |
| 2013/0345739 A1 | 12/2013 | Brady et al. | |
| 2014/0005712 A1 | 1/2014 | Martin et al. | |
| 2014/0046133 A1 | 2/2014 | Nakamura et al. | |
| 2014/0155980 A1 | 6/2014 | Turjman et al. | |
| 2014/0257253 A1 | 9/2014 | Jemison | |
| 2014/0276403 A1 | 9/2014 | Follmer et al. | |
| 2014/0330286 A1 | 11/2014 | Wallace | |
| 2014/0336691 A1 | 11/2014 | Jones et al. | |
| 2014/0364896 A1 | 12/2014 | Consigny | |
| 2014/0371779 A1 | 12/2014 | Vale et al. | |
| 2015/0005781 A1 | 1/2015 | Lund-Clausen et al. | |
| 2015/0005792 A1 | 1/2015 | Ahn | |
| 2015/0018859 A1 | 1/2015 | Quick et al. | |
| 2015/0018860 A1 | 1/2015 | Quick et al. | |
| 2015/0088190 A1 | 3/2015 | Jensen | |
| 2015/0164523 A1 | 6/2015 | Brady et al. | |
| 2015/0164666 A1 | 6/2015 | Johnson et al. | |
| 2015/0190155 A1 | 7/2015 | Ulm, III | |
| 2015/0190156 A1 | 7/2015 | Ulm, III | |
| 2015/0196380 A1 | 7/2015 | Berrada et al. | |
| 2016/0022293 A1 | 1/2016 | Dubrul et al. | |
| 2016/0058540 A1 | 3/2016 | Don Michael | |
| 2016/0074627 A1 | 3/2016 | Cottone | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113664 A1 | 4/2016 | Brady et al. | |
| 2016/0113665 A1 | 4/2016 | Brady et al. | |
| 2017/0086864 A1 | 3/2017 | Greenhalgh et al. | |
| 2017/0100142 A1 | 4/2017 | Look et al. | |
| 2017/0105743 A1 * | 4/2017 | Vale | A61B 17/221 |
| 2017/0112513 A1 | 4/2017 | Marchand et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |

(56) References Cited

U.S. PATENT DOCUMENTS

| | | | |
|---|---|---|---|
| 2017/0303948 | A1 | 10/2017 | Wallace et al. |
| 2017/0348014 | A1 | 12/2017 | Wallace et al. |
| 2018/0042624 | A1 | 2/2018 | Greenhalgh et al. |
| 2018/0042626 | A1 | 2/2018 | Greenhalgh et al. |
| 2018/0070968 | A1 | 3/2018 | Wallace et al. |
| 2019/0117244 | A1 | 4/2019 | Wallace et al. |
| 2019/0133622 | A1 | 5/2019 | Wallace et al. |
| 2019/0133623 | A1 | 5/2019 | Wallace et al. |
| 2019/0133624 | A1 | 5/2019 | Wallace et al. |
| 2019/0133625 | A1 | 5/2019 | Wallace et al. |
| 2019/0133626 | A1 | 5/2019 | Wallace et al. |
| 2019/0133627 | A1 | 5/2019 | Wallace et al. |
| 2019/0336148 | A1 | 11/2019 | Greenhalgh et al. |

FOREIGN PATENT DOCUMENTS

| | | |
|---|---|---|
| GB | 2498349 | 7/2013 |
| WO | WO 00/32118 | 6/2000 |
| WO | WO 2009086482 | 7/2009 |
| WO | WO 2012009675 | 1/2012 |
| WO | WO 2012049652 | 4/2012 |
| WO | WO 2012162437 | 11/2012 |
| WO | WO 2017058280 | 4/2017 |
| WO | WO 2017189535 | 11/2017 |
| WO | WO 2017189550 | 11/2017 |
| WO | WO 2017189591 | 11/2017 |
| WO | WO 2017189615 | 11/2017 |
| WO | WO 2017210487 | 12/2017 |
| WO | WO 2018049317 | 3/2018 |
| WO | WO 2019010318 | 1/2019 |
| WO | WO 2019094456 | 5/2019 |
| WO | WO 2019222117 | 11/2019 |

OTHER PUBLICATIONS

PCT International Search Report and Written Opinion for International Appln. No. PCT/US2017/029440, Applicant Stryker Corporation, dated Jul. 7, 2017.
PCT Invitation to Pay Additional Fees for International Appln. No. PCT/US2017/029366, Applicant Stryker Corporation, dated Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.
PCT Invitation to Pay Additional Fees for International Appln. No. PCT/US2017/029345, Applicant Stryker Corporation, dated Oct. 17, 2017.
Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Response to Non-Final Office Action for U.S. Appl. No. 14/496,786, filed Feb. 1, 2018.
Non-final office action dated Feb. 1, 2018 for U.S. Appl. No. 15/496,668.
Response to Restriction for U.S. Appl. No. 15/496,668, filed Feb. 21, 2018.
International search report and written opinion dated Feb. 28, 2018 for PCT/US2017/029345, Applicant Stryker Corporation 26 pages.
Notice of Allowance dated Mar. 22, 2018 for U.S. Appl. No. 15/496,668.
Notice of Allowance dated Apr. 19, 2018 for U.S. Appl. No. 15/496,570.
Notice of Allowance dated Apr. 19, 2018 for U.S. Appl. No. 15/496,786.
Non-Final Office Action dated Sep. 5, 2018 for U.S. Appl. No. 15/291,015.
Extended European Search Report dated Aug. 22, 2018 for European patent appln No. 16852212.6.
Extended European Search Report dated Oct. 5, 2018 for European patent appln No. 18174891.4.
Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
International search report and written opinion dated Nov. 14, 2018 for PCT/US2018/040937, Applicant Stryker Corporation 16 pages.
Notice of Allowance dated Dec. 11, 2018 for U.S. Appl. No. 15/291,015.
Invitation to Pay Additional Fees for International Patent Appln. No. PCT/US2018/059607 dated Jan. 31, 2019.
Japanese Office action dated Mar. 19, 2019 for Japanese Application No. 2018-535810 (with English Language translation).
International Search Report and Written Opinion dated Mar. 28, 2019 for International Appln. No. PCT/US2018/059607.
Notice of Allowance dated Apr. 10, 2019 for U.S. Appl. No. 15/611,546.
Response to Extended European Search Report for EP Patent Appln. No. 16852212.6 dated Mar. 15, 2019.
European Patent Office Communication Rule 161(1) and 162 dated Feb. 5, 2019 for EP Patent Appln. No. 17729703.3.
European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.
Response to European Patent Office Communication Rule 161(1) and 162 EPC filed Jun. 11, 2019, for EP Patent Appln. No. 17737084.8.
Response to European Patent Office Communication Rule 161(1) and 162 filed Jun. 4, 2019 for EP Patent Appln. No. 17722277.5.
Response to European Patent Office Communication Rule161(1) and 162 filed Jun. 4, 2019 for EP Patent Appln. No. 17722290.8.
Response to European Patent Office Communication 161(1) and 162 filed Jun. 11, 2019 for EP Patent Appln. No. 17721036.6.
European Patent Office Communication Rule161(1) and 162 dated Apr. 23, 2019 for EP Patent Appln. No. 17772186.7.
Response to Non-Final Office Action filed Nov. 8, 2017 for U.S. Appl. No. 15/496,570.
Response to Non-Final Office Action filed Feb. 1, 2018 for U.S. Appl. No. 15/496,786.
Restriction Requirement dated Apr. 11, 2019 for U.S. Appl. No. 15/497,092.
Response to Restriction Requirement filed Jun. 11, 2019 for U.S. Appl. No. 15/497,092.
Ex Parte Quayle office action mailed Jul. 16, 2019 for U.S. Appl. No. 15/497,092.
Response to Rule 161(1) and 162 EPC filed on Jul. 23, 2019 for EP application No. 17729703.3.
PCT International Search Report and Written Opinion for International Patent Appln. No. PCT/US2019/032601, Applicant Stryker Corporation, dated Jul. 23, 2019 (12 pages).
Response to Restriction Requirement filed Jul. 25, 2019 for U.S. Appl. No. 15/700,685.

(56) References Cited

OTHER PUBLICATIONS

Response to Ex Parte Quayle office action filed Jul. 25, 2019 for U.S. Appl. No. 15/497,092.
Office action dated Jun. 5, 2019 for Chinese application No. 2019053101871820, including partial English language translation provided by the foreign associate.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; ©2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 2 pgs.; retrieved/printed: Mar. 24, 2016.
Youtube; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
Notice of Allowance for U.S. Appl. No. 15/043,996 dated Jun. 9, 2016.
Ex Parte Quayle office action mailed Aug. 2, 2019 for U.S. Appl. No. 15/497,092.
Non Final Office Action dated Aug. 23, 2019 for U.S. Appl. No. 15/700,685.
Non Final Office Action dated Sep. 3, 2019 for U.S. Appl. No. 15/794,939.
Rule 71(3) Allowance for EP Patent Appln. No. 18174891.4 dated Jul. 30, 2019.
Response to Ex Parte Quayle office action filed Sep. 17, 2019 for U.S. Appl. No. 15/497,092.
Office action response filed on Sep. 26, 2019 for Chinese Patent Application No. 2016800567527, no translation received.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule161(1) and 162 filed Oct. 17, 2019 for EP Patent Appl. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.
Notice of Allowance dated Oct. 24, 2019 for U.S. Appl. No. 15/611,546.
Response to Non Final Office Action filed Nov. 8, 2019 for U.S. Appl. No. 15/700,685.
Notice of Allowance dated Nov. 6, 2019 for U.S. Appl. No. 15/795,097.
Rule 71(3) Allowance for EP Patent Appln. No. 17721036.6 dated Oct. 23, 2019.
Rule 71(3) Allowance for EP Patent Appln. No. 17722290.8 dated Nov. 11, 2019.
Notice of Allowance dated Nov. 21, 2019 for U.S. Appl. No. 15/700,685.
Amendment Response submitted on Dec. 3, 2019 for U.S. Appl. No. 15/794,939.
PCT International Search Report and Written Opinion for International Patent Appln. No. PCT/US2019/050467, Applicant Stryker Corporation, dated Dec. 18, 2019 (17 pages).
Final Office Action dated Mar. 2, 2020 for U.S. Appl. No. 15/794,939.
Notice of Allowance for U.S. Appl. No. 15/794,939 dated Mar. 31, 2020.
Amendment Response submitted on Mar. 27, 2020 for U.S. Appl. No. 16/594,256.
Non-Final Office Action for U.S. Appl. No. 16/096,031 dated May 8, 2020.
Non-Final Office Action for U.S. Appl. No. 16/183,162 dated May 13, 2020.
Non-Final Office Action for U.S. Appl. No. 16/169,334 dated May 8, 2020.
Non-Final Office Action for U.S. Appl. No. 16/183,171 dated May 13, 2020.
Foreign OA for Japanese Patent Application No. 2018-535810 dated Feb. 7, 2020.
Extended European Search Report for EP Patent Appl. No. 20185092.2 dated Sep. 11, 2020.
EP Examination Report for EP Patent Appl. No. 18745794.0 dated Jul. 20, 2020.
Amendment Response to Non-Final Office Action for U.S. Appl. No. 16/183,171 dated Jul. 30, 2020.
Amendment Response to Non-Final Office Action for U.S. Appl. No. 16/183,162 dated Jul. 30, 2020.
Applicant Interview Summary for U.S. Appl. No. 16/096,031 dated Jul. 30, 2020.
Applicant Interview Summary for U.S. Appl. No. 16/169,334 dated Jul. 30, 2020.
Applicant Interview Summary for U.S. Appl. No. 16/183,133 dated Aug. 24, 2020.
Non-Final Office Action for U.S. Appl. No. 16/183,149 dated Aug. 18, 2020.
Amendment Response to NFOA for U.S. Appl. No. 16/183,149 dated Sep. 25, 2020.

* cited by examiner

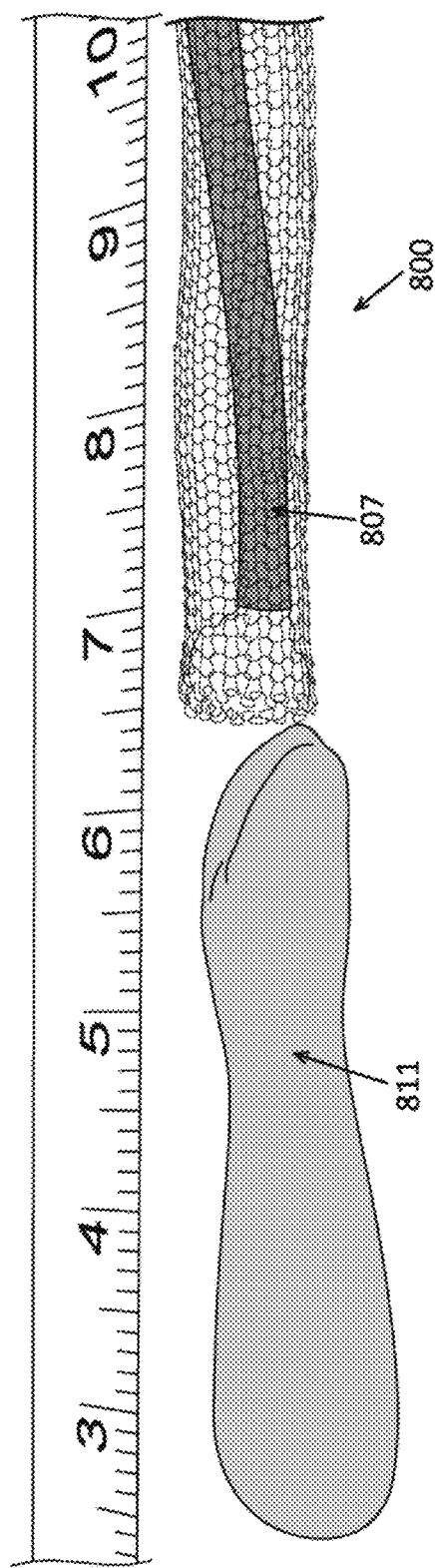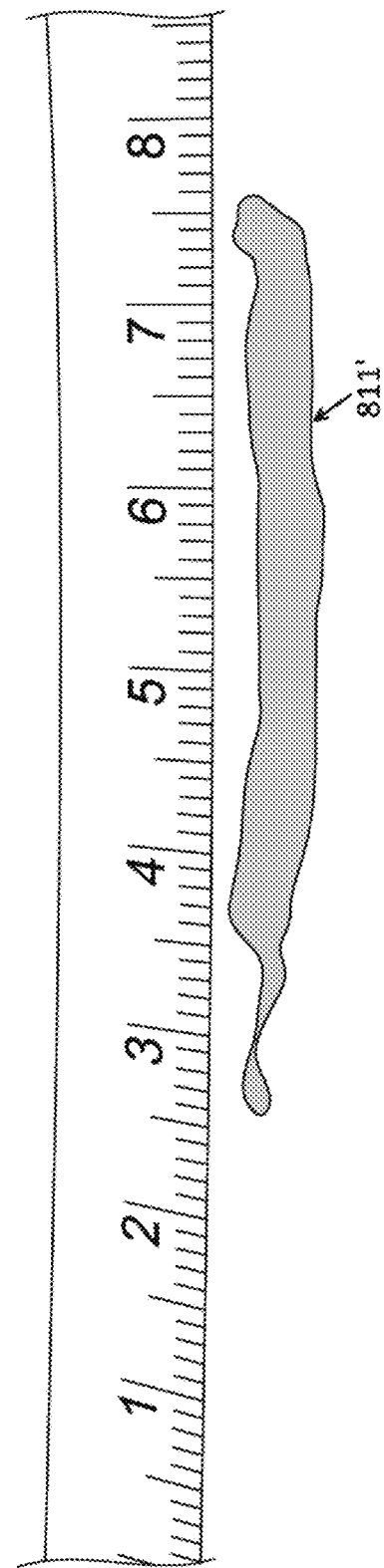
FIG. 8A
FIG. 8B

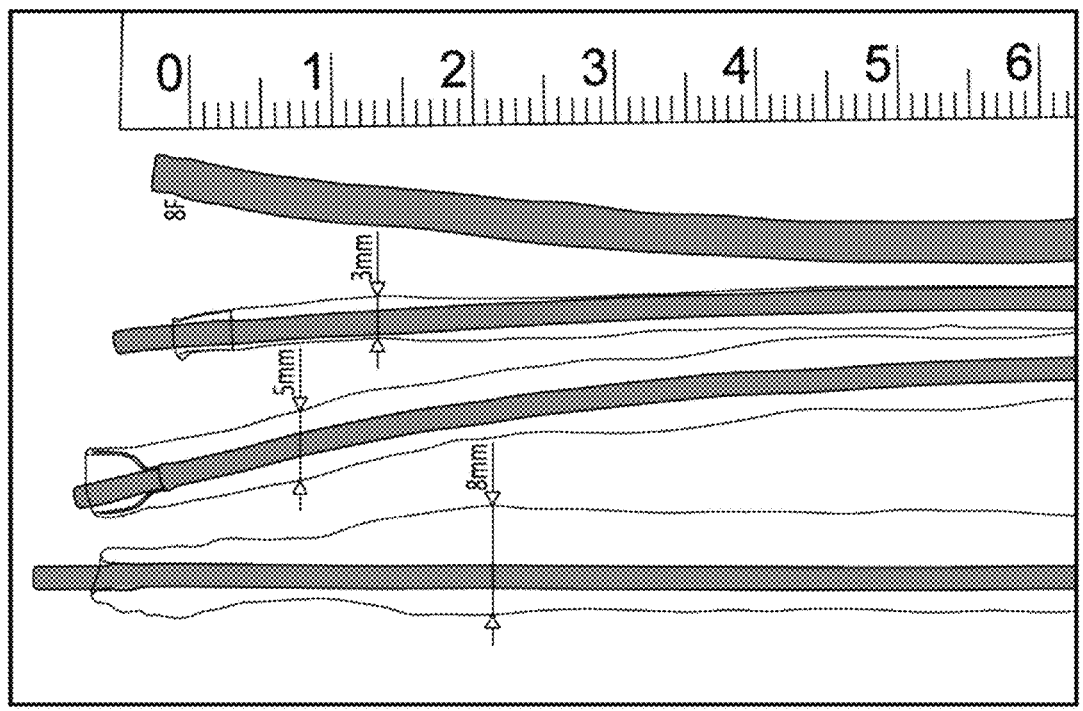
FIG. 9A
FIG. 9C
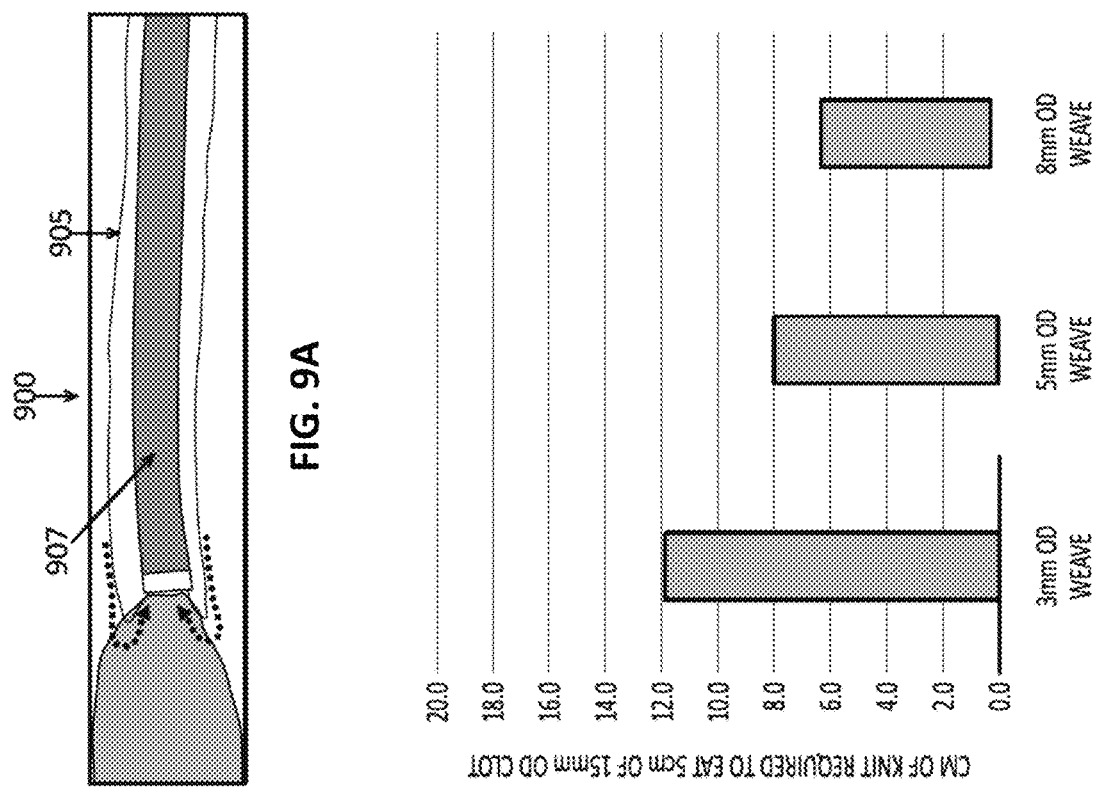
FIG. 9B

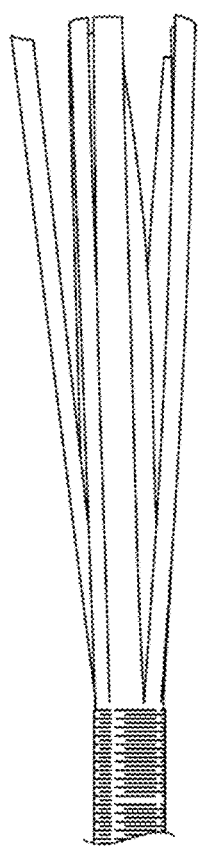
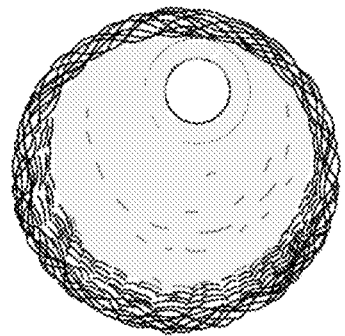
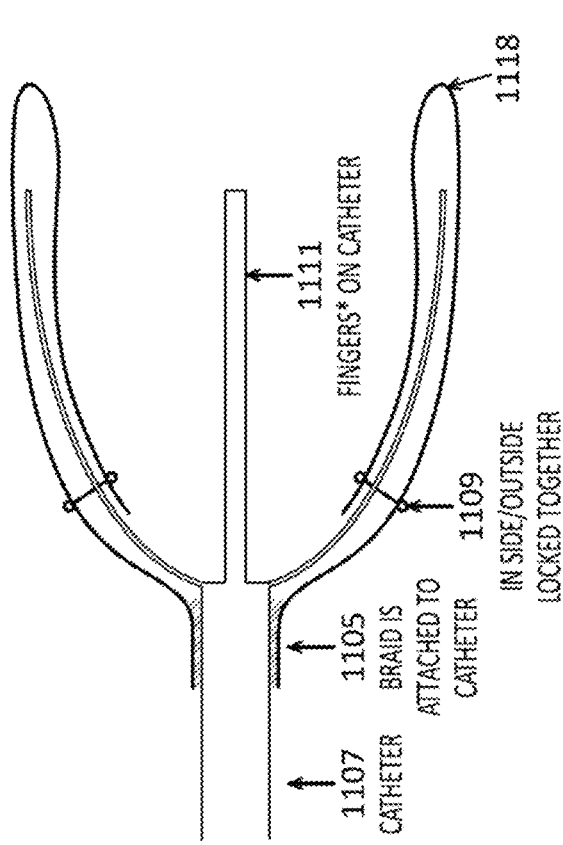
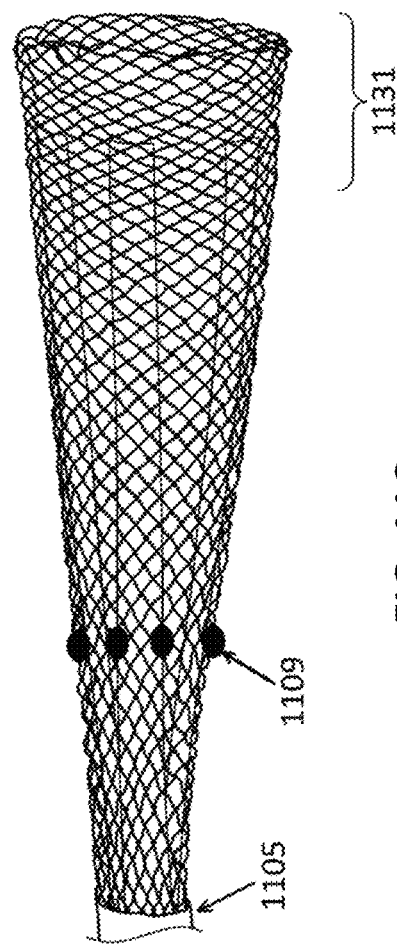

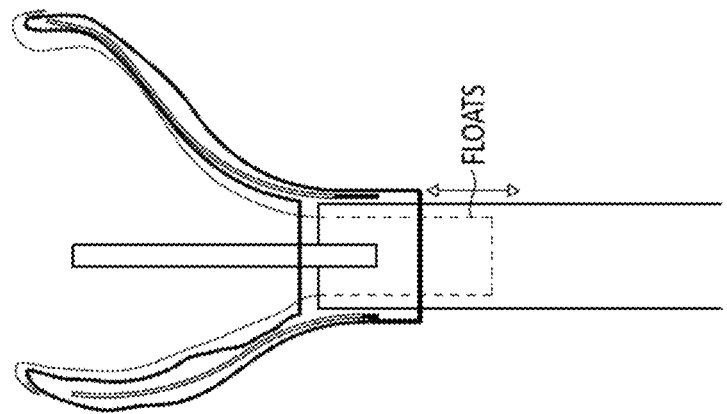
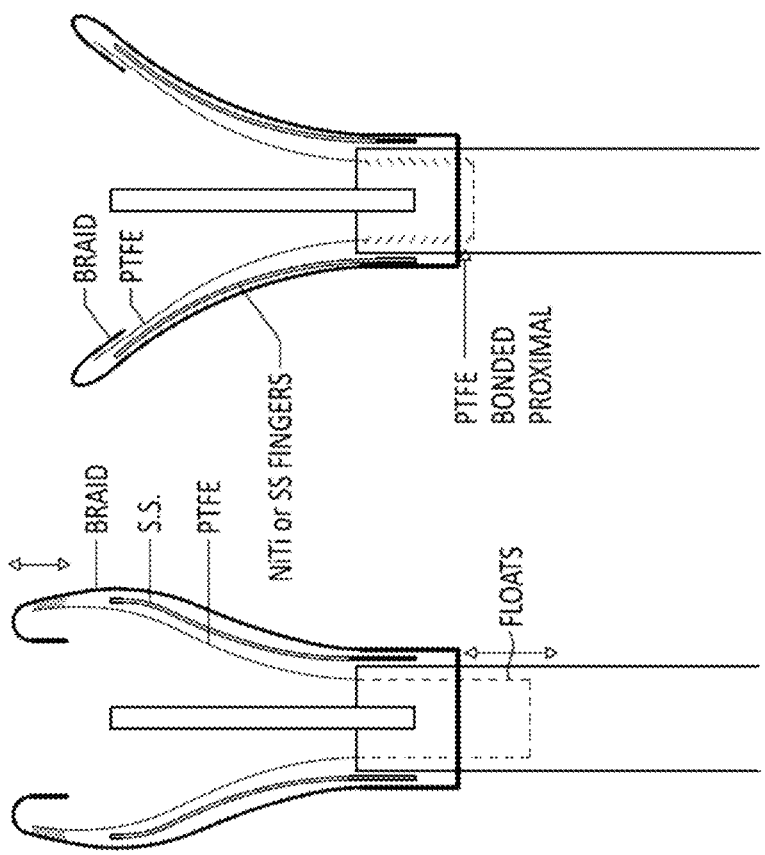
FIG. 14A  FIG. 14B  FIG. 14C

6F Thrombectomy Device
4-10 mm vessels

- ≤ 6F platform may be used for arterial approaches
- Funnel tip version of 5F device – 4mm OD funnel 6F – w/ 4mm Funnel

5F Thrombectomy Device
2-6 mm vessels

- Focused on arterial & venous below the knee
- No funnel on catheter tip

5F – No Funnel

- ≤ 8F (may be used for venous)
- Funnel tipped catheter – 8mm OD funnel

- Similar design to 8F funnel tipped version but with 10F size and larger funnel

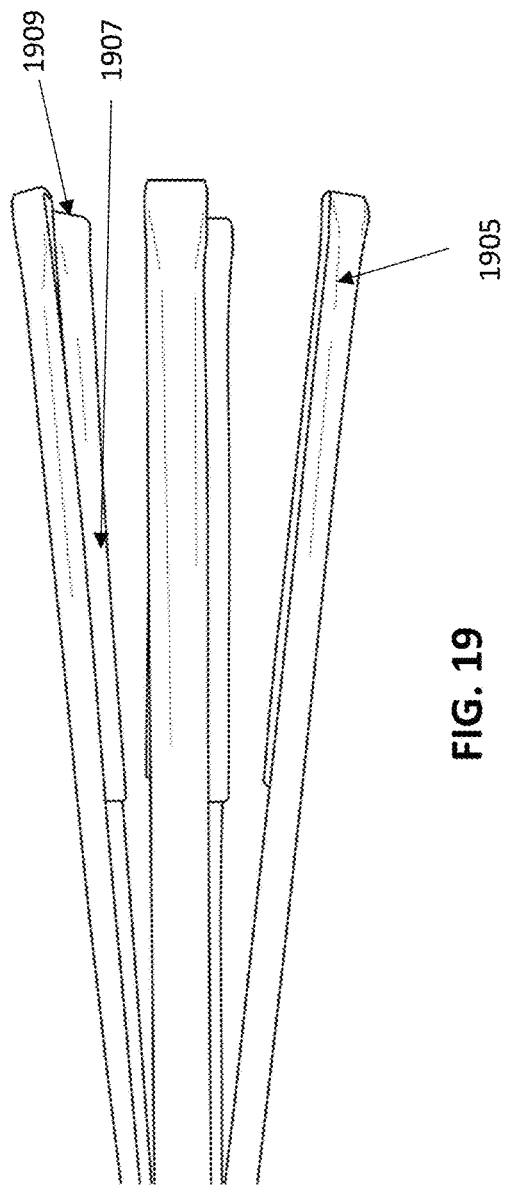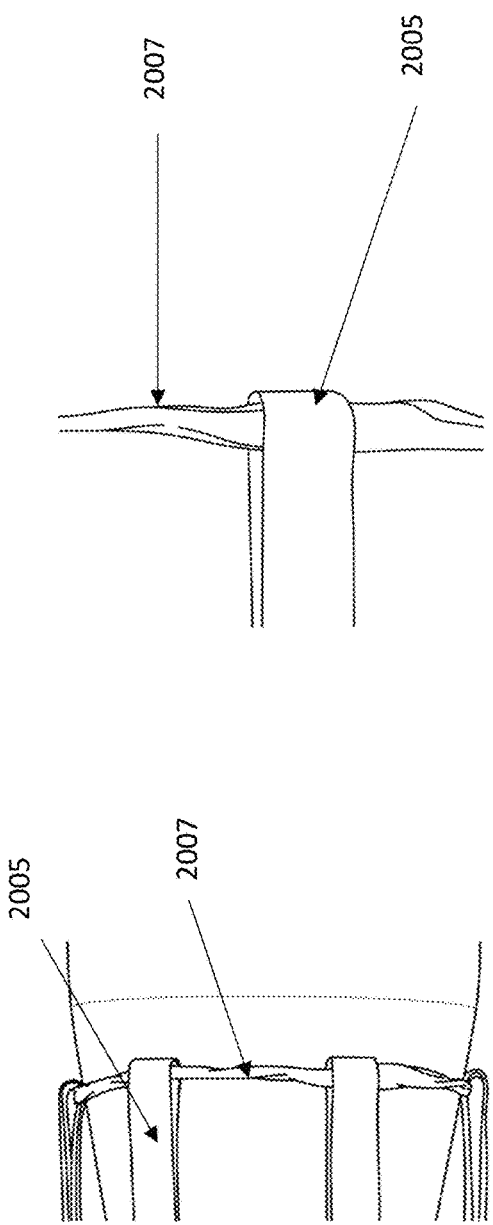

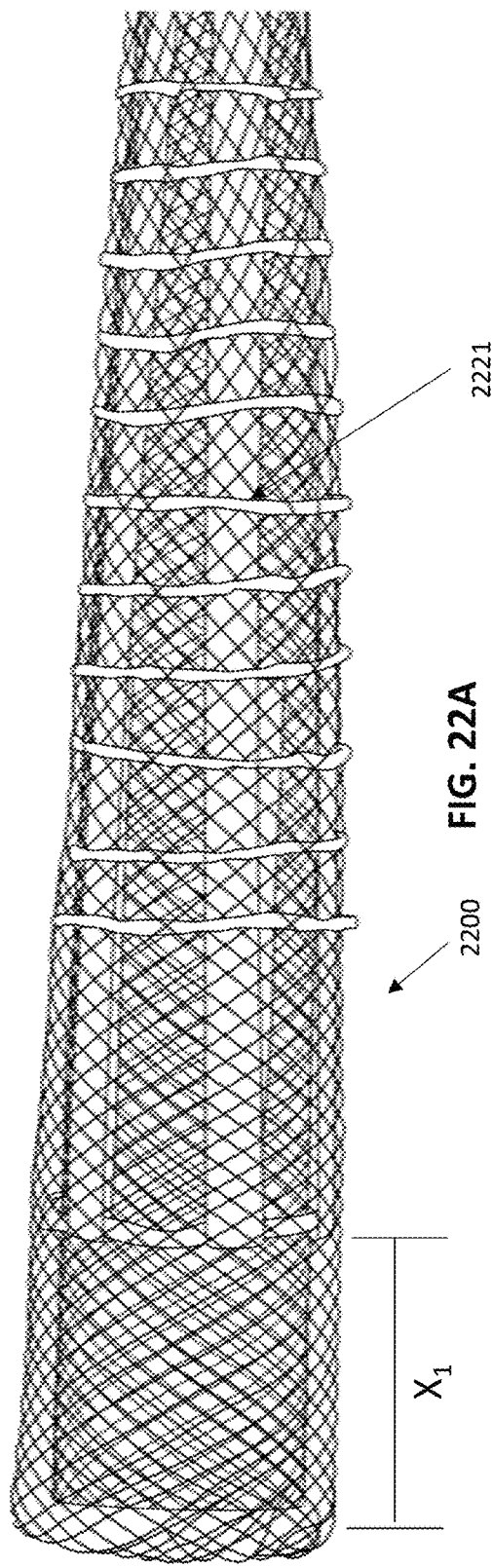
FIG. 22A
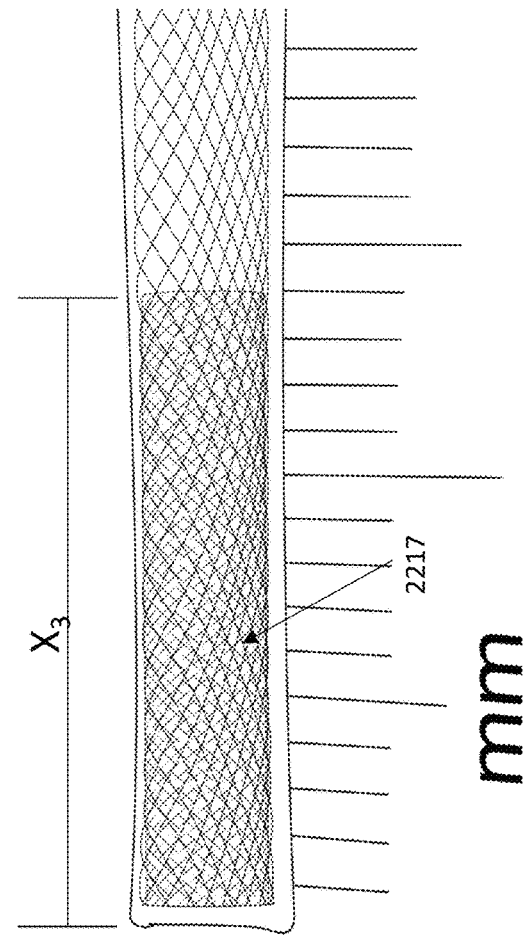
FIG. 22C
FIG. 22B

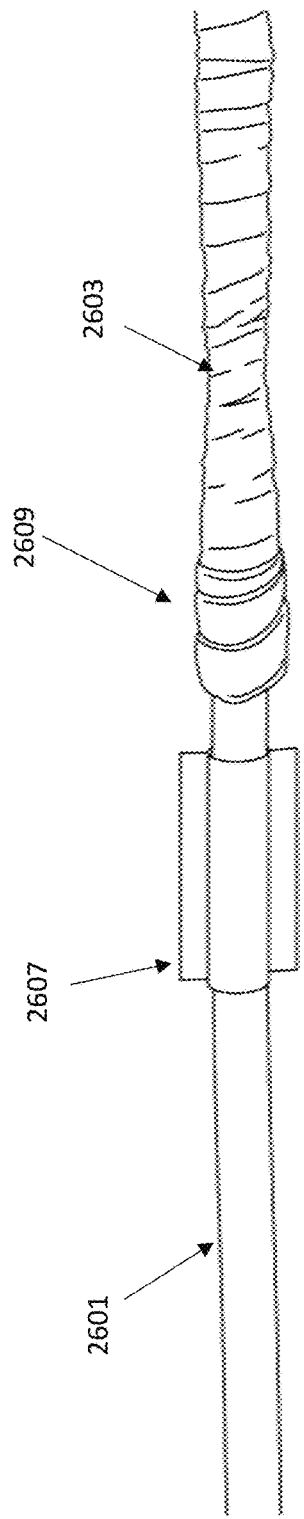
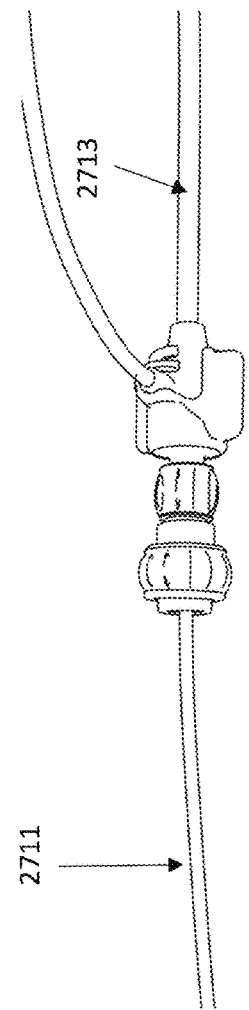
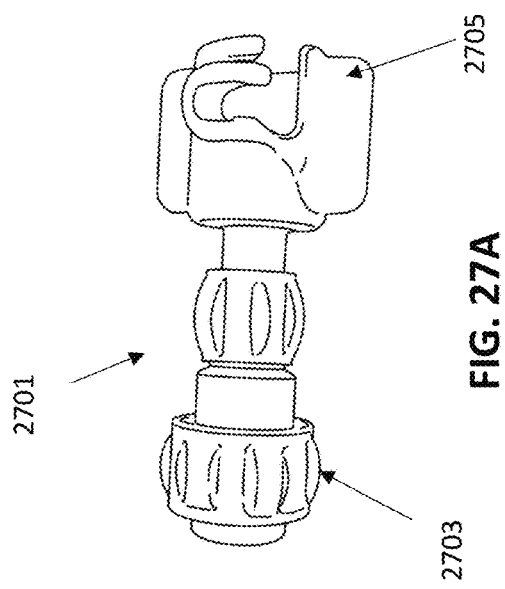
FIG. 26
FIG. 27A
FIG. 27B

INVERTING THROMBECTOMY APPARATUSES AND METHODS OF USE

CROSS REFERENCE TO RELATED APPLICATIONS

The present application is a continuation of PCT/US2019/050467, having an international filing date of Sep. 10, 2019, which claims priority to U.S. provisional patent application No. 62/729,276, titled "INVERTING THROMBECTOMY APPARATUSES FOR REMOVAL OF LARGE CLOTS," filed on Sep. 10, 2018, which are herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to mechanical removal of objects from within a body. In particular, described herein are mechanical thrombectomy apparatuses and methods.

BACKGROUND

Many vascular problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery. It is often desirable to remove tissue from the body in a minimally invasive manner as possible, so as not to damage other tissues. For example, removal of tissue, such as blood clots, from within a patient's vasculature may improve patient conditions and quality of life.

Mechanical thrombectomy devices may be particularly advantageous. There is a definite need for thrombectomy devices, and particularly for mechanical thrombectomy devices that can be easily and accurately delivered through the, often tortious, anatomy in the peripheral and central vasculature, then be reliably deployed to remove clot material. Further, there is a need for devices that are easy and intuitive to operate.

Finally, there is a distinct need for mechanical thrombectomy apparatuses that may have a low profile, but can be inserted into a comparatively large-diameter vessel. Thus, described herein are apparatuses (devices, systems and kits) and methods of using them that may address the needs and problems discussed above.

SUMMARY OF THE DISCLOSURE

Described herein are mechanical thrombectomy apparatuses (devices, systems, etc.) and methods of using and making them. These apparatuses may also be referred to as inverting mechanical thrombectomy apparatuses and/or inverting tube thrombectomy apparatuses. In particular, described herein are inverting tube thrombectomy apparatuses that may be deployed within even very large vessels in order to efficiently ingest one or more large clots. For example, the apparatuses described herein may be configured to provide a high pulling efficiency in order to ingest and remove even long and large-diameter clots, e.g., greater than 10 mm length and/or greater than 5 mm diameter, in a catheter having a smaller or much smaller diameter (e.g., 5 mm, 4 mm, 3 mm, 2 mm, etc.) using a flexible tube (e.g., tractor tube). In some variations the flexible tube may be longer than 5× the length of the clot (e.g., alternatively requiring a tractor tube that is longer than 6×, 7×, 8×).

In particular, described herein are apparatuses that may include an expandable funnel on the end of an inversion support catheter over which a flexible tube (e.g., tractor tube or simply tractor) rolls to invert. The flexible tube may be a knitted, or woven material. The flexible tube may generally have a first end coupled at a distal end region of a puller (which may be an elongate wire, tube, cannula, etc.), and the flexible tube may be arranged to invert over a distal end of the inversion support catheter at the funnel so that an external portion of the flexible tube extends proximally over the inversion support catheter as the internal (inverted) portion of the flexible tube is drawn into the funnel, compressing and removing fluid from the clot that is held by (e.g., grabbed by) the flexible tube, and pulling the inverted flexible tube into the inversion support catheter until the entire clot is captured, compressed and drawn into the outer catheter. The configuration of the apparatuses described herein are particularly well suited to grabbing and removing clot, and particularly large diameter clots, by using an inversion support catheter than includes an expandable funnel at the distal end. The collapsible/expandable funnel may configured to operate with the compressive forces applied by pulling the flexible tube into the inversion support catheter so that it inverts into the inversion support catheter, capturing the clot. The collapsible/expandable funnel may be configured to assume a fully expanded, locked (e.g., "jammed") configuration when the flexible tube applies a laterally compressive force on the distal end face of the funnel. Further, the funnel may include openings (described herein as having a porous structure) through which fluid squeezed out of the clot may exit laterally out of the funnel as the clot is moved into the narrower-diameter lumen of the inversion support catheter and compresses the clot. For example, the openings through the collapsible/expandable funnel (which may be referred to herein as simply an expandable funnel) that permit fluid to laterally leave the funnel walls as the clot is compressed may also prevent clogging or jamming of the clot.

In general, any of these apparatuses (e.g., systems) described herein may include: an inversion support catheter having an elongate and flexible body, the inversion support catheter having an expandable funnel at a distal end of the elongate and flexible body, wherein at least a portion of the expandable funnel at a proximal end of the expandable funnel, e.g., adjacent to the elongate flexible body, includes openings to allow fluid from the clot pass laterally out of the funnel wall (e.g., the funnel may be porous or partially porous). The apparatus may also include a flexible tube (e.g., "tractor"). The tractor may be woven or knit. In some variations the apparatus includes a puller within a lumen of the inversion support catheter; a first region of the puller at or near the distal end may be attached to the flexible tube. A second region of the flexible tube may extend over an outer surface of the elongate and flexible body. The system may be configured so that as the flexible tube inverts over a distal end of the expandable funnel, by pulling the flexible tube proximally into the inversion support catheter (e.g., by pulling the puller or on the first end of the flexible tube), the funnel may be fully extended to a locked (jammed) configuration, allowing the flexible tube to roll and invert over the open distal end (e.g., the distal edge) of the expandable funnel. This rolling motion of the flexible tube as well as the structure (e.g., woven, knit, etc.) of the flexible tube may capture clot and draw it into the lumen of the inversion support catheter, compressing the clot and removing fluid from it as it is pulled into the lumen. The first region of the flexible tube may be an end region of the flexible tube. The second end region of the flexible tube may be an end region.

In any of these apparatuses, a delivery catheter (also referred to herein as an intermediate catheter) may be used to help deploy the inversion support catheter and flexible tube assembly to the region of the vasculature including the clot or clots to be removed. For example, a system may include: an intermediate catheter; an inversion support catheter within the intermediate catheter, the inversion support catheter having an elongate and flexible body, the inversion support catheter having an expandable funnel at a distal end of the elongate and flexible body, the expandable funnel having a porous region at a proximal end of the expandable funnel adjacent to the elongate flexible body; a puller within a lumen of the inversion support catheter; and a flexible tube that is woven, the flexible tube having a first region attached to the puller within the inversion support catheter and a second region extending over an outer surface of the elongate and flexible body, wherein the flexible tube inverts over a distal end of the expandable funnel, further wherein the flexible tube is configure to be pulled proximally into the inversion support catheter by pulling the puller proximally so that the second region rolls and inverts over the distal end of the expandable funnel as it is pulled into the inversion support catheter.

Any of these systems may include an inner diameter of the second region of the flexible tube extending over the outer diameter of the elongate and flexible body that is greater than a maximum outer diameter of the expandable funnel in the expanded configuration. The system of any of these claims may have a base region of the expandable funnel adjacent to the distal end of the elongate and flexible body is porous. For example, the expandable funnel may comprise a circumferential porous region at a base of the expandable funnel adjacent to the distal end of the elongate and flexible body.

In any of these systems the collapsed configuration may have a maximum outer diameter of less than about 0.3× an outer diameter of the elongate and flexible body and/or a maximum outer diameter of less than about 8 mm.

The expanded configuration may have a minimum outer diameter of greater than about 2× an outer diameter of the elongate and flexible body. For example, the expanded configuration may have an outer diameter of between about 2 and about 26 mm.

In any of the systems described herein the flexible tube may comprise a knitted tube. In some variations the flexible tube may be formed of a woven material or a sheet of material (e.g., that has been laser cut). The tube may be formed from a strand or a filament (e.g., monofilament or multiple filaments). For example, the flexible tube may comprise a knitted tube having greater than 10 loops per transverse section through the knitted tube along a long axis of the knitted tube.

In general, the expandable funnel may be formed of a sheet of material, a woven, braided and/or knitted material and may include one or more supports (arms, struts, etc.).

For example, the expandable funnel may be a mesh that inverts over itself at the distal end of the expandable funnel.

In some variations, the expandable funnel comprises a plurality of longitudinal tines that are continuous with the elongate and flexible body. The expandable funnel may be self-expanding (e.g., biased at least partially open); alternatively or additionally the expandable funnel may be configured to expand when the first region of the flexible tube is pulled proximally. In some variations the expandable funnel may be configured to be self-expanding and to achieve a self-expanded configuration in an unconstrained configuration.

In general, the expandable funnels are integrated into the rest of the inversion support catheter to which they form a part. Thus, the interior of the expandable funnel is typically in fluid communication with the lumen of the rest of the catheter, and the catheter lumen may include the interior of the funnel. Similarly, the outside surface of the catheter body includes and encompasses the outside surface of thee funnel unless the context specifies otherwise.

Any of these apparatuses may include a lubricious sleeve over at least a portion of the expandable funnel. For example, the lubricious sleeve may be over the distal end region of the interior of the expandable funnel. In some variations the lubricious sleeve extends over the distal end of the funnel. In some variation the lubricious sleeve includes one or more openings; these openings may be in the proximal portion (e.g., near the base of the expandable funnel).

In general, the expandable funnel may be any appropriate size in the expanded configuration, e.g., having a maximum outer diameter of between 2-26 mm. For example, the expanded configuration may have a maximum outer diameter of greater than 16 mm (e.g., greater than about 2 mm, 3 mm, 4 mm, 5 mm, 6 mm, 7 mm, 8 mm, 9 mm, 10 mm, 12 mm, 14 mm, 16 mm, 18 mm, 20 mm, etc.). A user may generally select the inversion support catheter having a maximum size that is within about 60% (e.g., about 70%, about 75%, about 80%, about 85%, about 90% about 95%, etc.) or more the inner diameter of the vessel (e.g., alternatively or additionally, the outer diameter of the clot to be removed) in which the device is to be used.

Any of the apparatuses (e.g., systems) described herein may include an intermediate catheter at least partially surrounding the inversion support catheter and/or a puller within a lumen of the inversion support catheter. For example, a second end of the flexible tube may be coupled to a distal end region of the puller. The first region is attached proximal to a distal end of the puller.

In general, the expandable funnels described herein may be configured to withstand a pulling force adequate to allow the flexible tube to invert, roll and pull a clot (even a very large-diameter clot) into the funnel, compress the clot (e.g., removing much of the fluid of the clot) and draw the compressed clot into the inversion support catheter body. For example, the expandable funnel may be configured to withstand greater than about 500 g of compressive force (e.g., greater than about 600 g, 700 g, 750 g, 800 g, 900 g, 1000 g, 1100 g, 1200 g, 1300 g, 1400 g, 1500 g, etc.) of compressive force without collapsing when the compressive force is directed axially (e.g., proximally). For example, the expandable funnel may be configured to withstand greater than 1200 g of compressive force without collapsing. In some variations the compressive force may result in a locking together or stacking of the funnel, particularly when the funnel is made of a woven, knitted or braided material. For example, with a woven funnel, the compressive force may jam the weave of the funnel material axially to increase the braid angle of the distal (wider) region increasing the column strength of the funnel.

For example, a thrombectomy system may include: an inversion support catheter having an elongate and flexible catheter body, a catheter lumen, and an expandable funnel disposed at a distal end of the catheter body, wherein a distal end of the funnel defines a distal opening in communication with an interior of the funnel and the catheter lumen, respectively; and a flexible tube inverting over the distal end of the funnel such that the flexible tube has a first region at least partially disposed within the interior of the funnel and a second region at least partially extending over an exterior of the funnel, wherein the flexible tube is configured to be pulled proximally into the catheter lumen by pulling the first region proximally so that the second region rolls over the distal end of the funnel as the flexible tube is pulled into the catheter lumen.

In some variations a thrombectomy system may include: an inversion support catheter having an elongate and flexible catheter body, a catheter lumen, and an expandable funnel disposed at a distal end of the catheter body, wherein a distal end of the funnel defines a distal opening in communication with an interior of the funnel and the catheter lumen, respectively, and wherein at least a proximal portion of the funnel adjacent to the catheter body comprises openings configured to allow fluid to pass therethrough; a puller disposed within the catheter lumen; and a flexible tube formed of a knitted or woven material, the flexible tube inverting over the distal end of the funnel and having a first region attached to the puller and a second region at least partially extending over an exterior surface of the funnel, wherein the flexible tube is configured to be pulled proximally into the catheter lumen by pulling the puller proximally so that the second region of the flexible tube passes through the funnel interior and into the catheter lumen, respectively.

A thrombectomy system may include: an inversion support catheter having an elongate and flexible catheter body, a catheter lumen, and an expandable funnel disposed at a distal end of the catheter body, wherein a distal end of the funnel defines a distal opening in communication with an interior of the funnel and the catheter lumen, respectively, and wherein at least a proximal end of the funnel adjacent to the catheter body comprises openings configured to allow fluid to pass therethrough; and a flexible tube that is knitted, the flexible tube inverting over the distal end of the funnel and having a first region at least partially disposed within the interior of the funnel and a second region at least partially extending over an exterior of the funnel, wherein the flexible tube is configured to be pulled proximally into the catheter lumen by pulling the first region of the flexible tube proximally so that the second region of the flexible tube rolls over the distal end of the funnel as it is pulled into the funnel interior and catheter lumen, respectively, and wherein the funnel is configured such that pulling the first region of the flexible tube proximally applies an axially load on the funnel that expands the funnel into an expanded and jammed configuration.

Also described herein are methods of removing a clot from a vessel using any of the apparatuses described herein. For example, a method of removing a clot from a vessel may include: advancing an inverting tube apparatus through a vessel until a distal end of the inverting tube apparatus is proximate to a clot, wherein the inverting tube apparatus comprises an inversion support catheter having an expandable funnel at a distal end of an elongate and flexible body, and a flexible tube having a first region within the inversion support catheter and a second region extending over an outer surface of the inversion support catheter; expanding the expandable funnel from a collapsed configuration into an expanded configuration within the vessel; and pulling the first region of the flexible tube proximally to roll the flexible tube over a distal end of the expandable funnel of the inversion support catheter so that the flexible tube inverts over the distal end of the expandable funnel, to capture the clot and pull the clot proximally into the inversion support catheter, wherein pulling the clot proximally into the inversion support catheter comprises compressing the clot and ejecting fluid from the clot laterally out of the inversion support catheter.

For example, a method of removing a clot from a blood vessel may include: advancing an inverting tube apparatus through the blood vessel until a distal end portion of the inverting tube apparatus is located proximate to the clot, wherein the inverting tube apparatus comprises an inversion support catheter having an elongate and flexible catheter body, an internal catheter lumen, and an expandable funnel disposed at a distal end of the catheter body, wherein a distal end of the funnel defines an opening in communication with an interior of the funnel and the catheter lumen, respectively, the inverting tube apparatus further comprising a flexible tube inverted over the distal end of the expandable funnel and having a first region at least partially disposed within the interior of the funnel, and a second region at least partially extending over an exterior surface of the funnel; expanding the funnel from a collapsed delivery configuration into an expanded configuration within the blood vessel proximate to the clot; and pulling the first region of the flexible tube proximally to thereby roll the second region of the flexible tube over the distal end of the funnel so that the flexible tube captures the clot and pulls the clot proximally into the respective funnel interior and catheter lumen.

Any of the methods of removing a clot from a vessel described herein may include using any of these apparatuses. For example, a method of removing a clot from a vessel may include: advancing an inverting tube apparatus through a vessel until a distal end of the inverting tube apparatus is proximate to a clot, wherein the inverting tube apparatus comprises an inversion support catheter having an expandable funnel at a distal end of an elongate and flexible body, and a flexible tube having a first region within the inversion support catheter and a second region extending over an outer surface of the inversion support catheter; expanding the expandable funnel from a collapsed configuration into an expanded configuration within the vessel; and pulling the first region of the flexible tube proximally to roll the flexible tube over a distal end of the expandable funnel of the inversion support catheter so that the flexible tube inverts over the distal end of the expandable funnel, to capture the clot and pull the clot proximally into the inversion support catheter, wherein pulling the clot proximally into the inversion support catheter comprises compressing the clot and ejecting fluid from the clot laterally out of the inversion support catheter.

Any of these methods may include selecting the size of the inverting tube apparatus based on the size of the vessel, as mentioned above. The user may therefore select from a variety of different sizes of the intermediate catheter and/or flexible tube based on the size of the vessel and/or clot.

In any of these methods, expanding may include expanding the expandable funnel to an outer diameter that is greater than at least $\frac{1}{3}$ the diameter of an outer diameter of the clot (e.g., greater than 33%, greater than 40%, greater than 50%, greater than 60%, greater than 70%, greater than 80%, greater than 90%, etc. of the OD of the clot and/or ID of the vessel). For example, expanding may comprise expanding the expandable funnel to an outer diameter that is greater than at least 50% the diameter of an outer diameter of the clot.

In some variations, pulling the clot proximally may comprise applying between 500 g and 3000 g of force.

In some variations, expanding the expandable funnel may comprise allowing the expandable funnel to self-expand in the vessel and/or expanding the expandable funnel may comprise applying an axial compressive force on the expandable funnel by pulling the first region of the flexible tube proximally. A self-expanding funnel may be further expanded by applying an axial compressive force on the expandable funnel by pulling the flexible tube proximally. For example, in some variations the expandable funnel may be configured to be self-expanding into a self-expanded configuration when unconstrained, e.g., when released from a constrained configuration within a second (e.g., guide catheter, intermediate catheter, etc.).

Any of these methods may include removing the flexible tube from within the inversion support catheter and reloading a new flexible tube into the inversion support catheter.

For example, described herein are systems, including thrombectomy systems. Any of these systems may include: an inversion support catheter having an elongate and flexible body, the inversion support catheter having an expandable funnel at a distal end of the elongate and flexible body; and a flexible tube having a first region within the inversion support catheter and a second region extending over an outer surface of the elongate and flexible body, wherein the flexible tube inverts over a distal end of the expandable funnel, further wherein the flexible tube is configure to be pulled proximally into the inversion support catheter by pulling the first region proximally so that the second region rolls and inverts over the distal end of the expandable funnel as it is pulled into the inversion support catheter.

Any of these systems may include: an inversion support catheter having an elongate and flexible body, the inversion support catheter having an expandable funnel at a distal end of the elongate and flexible body, wherein at least a proximal end of the expandable funnel adjacent to the elongate flexible body comprises openings configured to allow fluid to pass; a puller within a lumen of the inversion support catheter; and a flexible tube formed of a knitted or woven material, the flexible tube having a first region attached to the puller within the inversion support catheter and a second region extending over an outer surface of the elongate and flexible body, wherein the flexible tube inverts over a distal end of the expandable funnel, further wherein the flexible tube is configure to be pulled proximally into the inversion support catheter by pulling the puller proximally so that the flexible tube rolls and inverts over the distal end of the expandable funnel as it is pulled into the inversion support catheter.

For example, a system may include: an inversion support catheter having an elongate and flexible body, the inversion support catheter having an expandable funnel at a distal end of the elongate and flexible body, further wherein at least a proximal end of the expandable funnel adjacent to the elongate flexible body comprises openings configured to allow fluid to pass; a puller within a lumen of the inversion support catheter; and a flexible tube that is knitted, the flexible tube having a first region attached to the puller within the inversion support catheter and a second region extending over an outer surface of the elongate and flexible body, wherein the flexible tube inverts over a distal end of the expandable funnel, further wherein the flexible tube is configure to be pulled proximally into the inversion support catheter by pulling the puller proximally so that the flexible tube rolls and inverts over the distal end of the expandable funnel as it is pulled into the inversion support catheter to apply an axially load on the funnel to expand the funnel into the expanded configuration.

In any of these systems, an inner diameter of the second region of the flexible tube extending over the outer diameter of the elongate and flexible body may be less than a maximum outer diameter of the expandable funnel in the expanded configuration. Thus, the flexible tube may be expanded as it is pulled over the funnel portion of the inversion support catheter from a narrower relaxed diameter over the more proximal body of the inversion support catheter. In any of the apparatuses described herein the flexible tube may be biased so that the inverted portion (when in the inversion support catheter) is self-expanded (or shape set to expand), e.g., to have an outer diameter that is 40% or greater than the inner diameter of the inversion support catheter elongate body (e.g., 50% or greater, 60% or greater, 70% or greater, 75% or greater, 80% or greater, etc.).

As mentioned, the base region of the expandable funnel adjacent to the distal end of the elongate and flexible body may include openings configured to allow fluid to pass (e.g., may be referred to as porous). The openings or pores in some variations may be formed by the openings between the one or more strands forming the woven funnel body. For example, the expandable funnel may include a circumferential porous region at a base of the expandable funnel adjacent to the distal end of the elongate and flexible body.

The collapsed configuration of the expandable funnel may have a maximum outer diameter of less than 0.3× (e.g., 30% of) the outer diameter of the elongate and flexible body. In some generations the collapsed configuration may be configured to collapse the distal end of the expandable funnel to 30% or less, 40% or less, 50% or less, 60% or less, 70% or less, 75% or less, 80% or less, etc. of the outer diameter of the elongate and flexible body of the inversion support catheter (e.g., the average outer diameter or the region of the inversion support catheter proximal to the funnel). In some variations the collapsed configuration has a maximum outer diameter of less than 8 mm.

In some variations the expanded configuration may have a minimum outer diameter of greater than 2× an outer diameter of the elongate and flexible body (e.g., greater than 2.5×, greater than 3×, greater than 3.5×, etc.). The maximum outer diameter is typically the diameter of the distal face of the funnel, which may also be referred to as the distal opening or distal edge. For example, the expanded configuration may have an outer diameter of between 2 and 26 mm.

As mentioned, in general, the flexible tube may include a knitted tube; for example, the flexible tube may be configured as a knitted tube having greater than 10 loops per transverse section through the knitted tube along a long axis of the knitted tube.

As described in greater detail below, the expandable funnel may include a plurality of longitudinal tines (e.g., struts) that are continuous with the elongate and flexible body. These tines may extend in a distal (e.g., longitudinal) direction and may be covered by, e.g., a mesh material (e.g., in some variations, a woven or knitted material) that is folded over itself to form an inner surface within the mouth of the funnel and an outer surface on the outside of the funnel. The tines may be inserted between the inner and outer surface and may be longitudinally movable relative to the inner and outer surface. For example, the expandable funnel may comprise a mesh inverted over itself at the distal end of the expandable funnel.

In general, the funnel may be biased to be at least partially self-expanding. In some variations, the expandable funnel is configured to fully expand when the first region of the flexible tube is pulled proximally.

In any of the apparatuses described herein a lubricious sleeve may be included over at least a portion of the expandable funnel; for example, over an inner and/or outer surface, and/or over the inverting distal end region.

The funnel may be configured to open to any appropriate diameter. For example, in some variations, the expandable funnel may have a maximum outer diameter of greater than 16 mm.

Any of the apparatuses described herein may include a puller (rod, catheter, wire, etc.) within a lumen of the inversion support catheter, wherein a second end of the flexible tube is coupled to a distal end region of the puller; in some variations the first region of the flexible tube may be attached proximal to a distal end of the puller.

In some variations a thrombectomy apparatus may include: an inversion support catheter having an expandable funnel at the distal end of a flexible elongate body, the expandable funnel comprising: a funnel surface formed of a first tube of knitted or woven material inverted over itself to form an inner funnel surface and an outer funnel surface, and a plurality of support tines extending distally between the inner funnel surface and the outer funnel surface, wherein the funnel surface is configured to slide axially relative to the plurality of support tines; and a second flexible tube of knitted or woven material extending distally along an outer surface of the inversion support catheter and inverting over and into the expandable funnel and into a lumen of the inversion support catheter, wherein the expandable funnel is configured to expand to a jammed configuration when the second flexible tube is pulled proximally into the inversion support catheter. As mentioned above, the funnel surface may comprise a woven material. In some variations, the funnel surface has a braid angle of greater than 90 degrees in the jammed configuration.

Thus, in some variations of the expandable funnel described herein, the expandable funnel may be configured to assume a jammed configuration when an axially compressive force is applied, e.g., by pulling the tractor (e.g., flexible tube) proximally so that it rolls, and inverts, from the outside of the inversion support catheter, over the funnel and into the lumen of the inversion support catheter. The jammed configuration may result in a compressed configuration in which the expandable funnel is stiffer than in an un-jammed configuration. The jammed configuration may also have a greater column strength. In variations in which the walls of the expandable funnel are formed from a woven material, the jammed configuration may result from the weave having a maximum braid angle, which may be referred to as the jamming angle.

As mentioned above, the plurality of tines may be formed (e.g., cut, such as laser cut) from the flexible elongate body. The expandable funnel may also include one or more circumferential supports extending radially around the funnel surface and constraining the outer diameter of the expandable funnel. The one or more circumferential supports may comprise a filament, e.g., one or more of: a yarn, a wire, a suture, and a thread. For example, the one or more circumferential supports may comprise a suture material. The one or more circumferential supports may connect the inner funnel surface to the outer funnel surface. The one or more circumferential supports may extend helically around the expandable funnel, as one, or in some cases more than one, filaments.

In some variations, the tines fold back on themselves and may be crimped together. In some variations each tine is connected, e.g., at the distal end region, by a filament. This filament may be referred to as a tine filament and may distribute force between the different tines. Multiple different tine filaments may be used. In some variations, the tine filament may be secured to the tines near the distal end of the tines (e.g., within 1 mm, 2 mm, 3 mm, etc.) from the distal-facing ends of the tines. In some variations the tine filament(s) are secured within the cavity formed by the folded over body of the tine.

In any of the expandable funnels described herein, the funnel surface may extend a relatively short distance from the distal end of the tines when the funnel is in the jammed and expanded configuration. For example the mesh forming the outer and inner surfaces, that may be secured to each other, but not to the tines, and the mesh may extend distally of the tines in the expanded configured to more than 5 mm or less (e.g., 4 mm or less, 3 mm or less, 2 mm or less, 1 mm or less, etc.) from a distal end of the plurality of tines when the expandable funnel is expanded to the jammed configuration. For example, the funnel surface may extend 1 mm or less from a distal end of the plurality of tines when the expandable funnel is expanded to the jammed configuration.

As described above, the second flexible tube may be formed of a knitted material. Further, any of the apparatuses described herein may include a puller extending through the inversion support catheter and coupled at a distal end to a first end of the second flexible tube. The funnel surface be shape-set so that that inner surface has a smaller outer diameter than the inner diameter of the outer surface, to create a space between the inner surface and the outer surface for the plurality of tines.

For example, described herein are thrombectomy apparatus that include: an inversion support catheter having an expandable funnel at the distal end of a flexible elongate body, the expandable funnel comprising: a funnel surface formed of a first tube of woven material inverted over itself to form an inner funnel surface and an outer funnel surface, a plurality of support tines extending distally between the inner funnel surface and the outer funnel surface, wherein the funnel surface is configured to slide axially relative to the plurality of support tines, and one or more circumferential supports extending radially around the funnel surface and constraining the maximum outer diameter of the expandable funnel; and a second flexible tube of knitted or woven material extending distally along an outer surface of the inversion support catheter and inverting over and into the expandable funnel and into a lumen of the inversion support catheter when a first end of the second flexible tube is pulled proximally into the inversion support catheter.

A thrombectomy apparatus may include: an inversion support catheter having an expandable funnel at the distal end of a flexible elongate body, the expandable funnel comprising: a funnel surface formed of a first tube of woven material inverted over itself to form an inner funnel surface and an outer funnel surface, a plurality of support tines extending distally between the inner funnel surface and the outer funnel surface, wherein the funnel surface is configured to slide axially relative to the plurality of support tines, and one or more circumferential supports extending radially around the funnel surface and constraining the maximum outer diameter of the expandable funnel and connecting the inner funnel surface to the outer funnel surface; and a second flexible tube of knitted or woven material extending distally along an outer surface of the inversion support catheter and inverting over and into the expandable funnel and into a lumen of the inversion support catheter when a first end of the second flexible tube is pulled proximally into the inversion support catheter.

In some variations, a thrombectomy apparatus may include: an inversion support catheter having an expandable funnel at the distal end of a flexible elongate catheter body, the funnel comprising a first flexible tube of knitted or woven material inverted over itself to form an inner funnel surface and an outer funnel surface, the inner funnel surface defining an interior of the funnel in communication with a lumen of the catheter extending through the catheter body, and a plurality of support tines extending distally from a distal end of the catheter body between the inner funnel surface and the outer funnel surface, wherein the respective inner funnel surface and outer funnel surface are configured to slide axially relative to the support tines; and a second flexible tube of knitted or woven material extending distally along at least a portion of an outer surface of the catheter body and the outer funnel surface, respectively, and inverting over a distal end of the funnel into an interior of the funnel and catheter lumen, respectively, wherein the funnel is configured to expand to a jammed configuration when the second flexible tube is pulled proximally into the catheter lumen.

The apparatuses described herein may be configured as kits or systems for performing a thrombectomy and may be packaged together, including pre-loading the component parts, or sold separately. For example, described herein are thrombectomy systems that may include: an inversion support catheter, the inversion support catheter having an elongate and flexible body and an expandable funnel at a distal end of the elongate and flexible body; a flexible tube of knitted or woven material extending distally along an outer surface of the inversion support catheter and configured to invert over and into the expandable funnel and into a lumen of the inversion support catheter to expand the expandable funnel; and a tear-away sleeve extending over the flexible tube and the inversion support catheter and configured to be removed from over the flexible tube by tearing along a length of the tear-away sleeve as the inversion support catheter and flexible tube are loaded into a delivery catheter.

A thrombectomy system may include: an inversion support catheter, the inversion support catheter having an elongate and flexible body and an expandable funnel at a distal end of the elongate and flexible body; a flexible tube of knitted or woven material extending distally along an outer surface of the inversion support catheter and configured to invert over and into the expandable funnel and into a lumen of the inversion support catheter to expand the expandable funnel; and a loading sleeve, wherein the distal end of the inversion support catheter is loaded into the loading sleeve so that the expandable funnel is constrained in a collapsed configuration, further wherein the loading sleeve comprises a tear-line configured to break apart loading sleeve for removing the loading sleeve from the inversion support catheter.

In some variations a thrombectomy system may include: an inversion support catheter, the inversion support catheter having an elongate and flexible body and an expandable funnel at a distal end of the elongate and flexible body; a flexible tube of knitted material extending distally along an outer surface of the inversion support catheter and configured to invert over and into the expandable funnel and into a lumen of the inversion support catheter to expand the expandable funnel; a loading sleeve, wherein the distal end of the inversion support catheter is loaded into the loading sleeve so that the expandable funnel is constrained in a collapsed configuration, further wherein the loading sleeve comprises a tear-line configured to break apart loading sleeve for removing the loading sleeve from the inversion support catheter; and a tear-away sleeve extending over the flexible tube and the inversion support catheter and configured to be removed from over the flexible tube by tearing along a length of the tear-away sleeve as the inversion support catheter and flexible tube are loaded into a delivery catheter.

Thus, any of the systems described herein may include a loading sleeve, wherein the distal end of the inversion support catheter is loaded into the loading sleeve so that the expandable funnel is constrained in a collapsed configuration.

Any of these systems may include a delivery catheter, wherein the loading sleeve is configured to be inserted into a proximal end of the delivery catheter so that the inversion support catheter and flexible tube of knitted or woven material may be driven distally into the delivery catheter.

In addition, any of these systems may include a second flexible tube of knitted or woven material configured to be inserted into the inversion support catheter. Thus, the system may be configured to allow deployment of a second flexible tube that may be configured (e.g., with a loading sleeve) for inserting and at least partially into an inversion support catheter, e.g., by the physician, nurse, medical technician, etc.

Any of the inversion support catheters described herein may include a stop at a proximal end region of the inversion support catheter that is configured to prevent the flexible tube of knitted or woven material from extending over the outer surface of the inversion support catheter proximally past the stop. This may be particularly useful when a flexible tube installed (e.g., by a user) over an inversion support catheter, and inserted into a delivery catheter; even with a tear-away sleeve preventing the flexible tube (which may be a knitted tube, for example) from pushing proximally as the inversion support catheter and flexible tube is pushed distally into the delivery catheter.

In some variations, the flexible tube may include an elastic cuff on a proximal end of the flexible tube of knitted or woven material; this elastic cuff may interact with (e.g., engage) the stop of the inversion support catheter and may prevent it from extending beyond the stop.

As already described above, the system may include a puller within the inversion support catheter, wherein a distal end of the flexible tube of knitted or woven material is coupled to the puller.

In some variations the system may include a lock configured to lock the inversion support catheter to a delivery catheter. The lock may engage with both the delivery catheter and the inversion support catheter so that the two may be moved together, e.g., with a single hand.

A thrombectomy system may include: an inversion support catheter, the inversion support catheter having an elongate and flexible catheter body, a catheter lumen, and an expandable funnel at a distal end of the catheter body, wherein a distal end of the funnel defines an opening in communication with an interior of the funnel and the catheter lumen, respectively; a first flexible tube of knitted or woven material extending distally along at least a portion of an outer surface of the catheter body and an outer surface of the funnel, respectively, wherein at least a portion of the first flexible tube inverts over the distal end of the funnel and into the respective funnel interior and catheter lumen, respectively; and a tear-away sleeve extending over the first flexible tube and at least a distal portion of the inversion support catheter, the tear-away sleeve configured to be removed from over the first flexible tube by tearing along a length of the tear-away sleeve as the inversion support catheter and first flexible tube are loaded into a delivery catheter.

For example, a thrombectomy system may include: an inversion support catheter, the inversion support catheter having an elongate and flexible catheter body, a catheter lumen, and an expandable funnel at a distal end of the catheter body, wherein a distal end of the funnel defines an opening in communication with an interior of the funnel and the catheter lumen, respectively; a first flexible tube of knitted or woven material extending distally along at least a portion of an outer surface of the catheter body and an outer surface of the funnel, respectively, wherein at least a portion of the first flexible tube inverts over the distal end of the funnel and into the respective funnel interior and catheter lumen, respectively; and a loading sleeve, wherein the distal portion of the inversion support catheter may be loaded into the loading sleeve with the funnel constrained in a collapsed configuration, and wherein the loading sleeve comprises a tear-line configured for breaking apart and removing the loading sleeve from over the inversion support catheter.

Although the inversion support catheters having an expandable funnel as described herein may be included as part of an apparatus for performing a thrombectomy (or an atherectomy in some variations) any of these inversion support catheters may find use by themselves, without the other components of the system (e.g., the flexible tube). For example, described herein are support catheters having an expandable funnel at the distal end of a flexible elongate body, the expandable funnel comprising: a funnel surface formed of a first tube of knitted or woven material inverted over itself to form an inner funnel surface and an outer funnel surface, and a plurality of support tines extending distally between the inner funnel surface and the outer funnel surface, wherein the funnel surface is configured to slide axially relative to the plurality of support tines.

As mentioned, also described herein are methods of performing an atherectomy using any of the apparatuses as described herein, in order to remove atheroma. In general the inverting tube apparatus may include or be used in conjunction with one or more ring cutters, such as a ring stripper or a double-ring cutter that may be used to transect the atheroma core. (e.g., a MollRing Cutter); a stent may then be inserted.

For example, described herein are atherectomy methods comprising: advancing an inverting tube apparatus through a vessel until a distal end of the inverting tube apparatus is proximate to an atheroma, wherein the inverting tube apparatus comprises an inversion support catheter having an expandable funnel at a distal end of an elongate and flexible body, the expandable funnel having a collapsed configuration and an expanded configuration, and a flexible tube having a first region within the inversion support catheter and a second region extending over an outer surface of the inversion support catheter; expanding the expandable funnel from a collapsed configuration into an expanded configuration within the vessel proximal to the atheroma; and pulling the first region of the flexible tube proximally to roll the flexible tube over a distal end of the expandable funnel of the inversion support catheter so that the flexible tube inverts over the distal end of the expandable funnel while advancing the inverting tube apparatus distally; applying an axial shearing force to the walls from the moving flexible tube to cut the atheroma from the vessel.

Applying the axial shearing force may further comprise rasping the atheroma with a plurality or projections extending from the flexible tube.

Any of these methods may further comprise advancing a ring cutter (or dual-ring cutter/stripper) over the inverting tube apparatus and into the atheroma after the inverting tube apparatus has engaged with the atheroma. The method may further comprise cutting the atheroma transversely to a long axis of the vessel with a second ring cutter by withdrawing the second ring cutter proximally.

For example, the apparatuses (e.g., systems, devices, etc.) and methods described herein may also be adapted for removing atheroma material, including performing an atherectomy. An apparatus as described herein configured as an atherectomy device may include: an inversion support catheter having an elongate and flexible body, the inversion support catheter having an expandable funnel at a distal end of the elongate and flexible body (e.g., having a collapsed configuration and an expanded configuration); and a flexible tube having a first region within the inversion support catheter and a second region extending over an outer surface of the elongate and flexible body, wherein the flexible tube inverts over a distal end of the expandable funnel, further wherein the flexible tube is configure to be pulled proximally into the inversion support catheter by pulling the first region proximally so that the second region rolls and inverts over the distal end of the expandable funnel as it is pulled into the inversion support catheter. The flexible tube may include atheroma capturing or cutting protrusions that may extend out from the flexible tube as it rolls over and into the funnel. For example, as the flexible tube moves along the outer ramp-like side of the funnel, the protrusions may be extended from the flexible tube to engage an atheroma. In some variations the flexible tube may be reciprocated in/out of the expandable funnel to cut and/or remove the atheroma.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 1A, the assembled apparatus is shown in a side view, showing an inversion support catheter and a flexible outer tube. FIG. 1B shows the inverting tube apparatus of FIG. 1A in a vessel, proximal to a clot. FIG. 1C illustrates the removal of a clot from the vessel using the apparatus of FIG. 1A, by pulling the flexible tube on the outside of the inversion support catheter proximally so that it rolls over the distal end of the inversion support catheter and into the inversion support catheter, drawing the clot with it; the apparatus may be advanced distally.

In FIG. 3A the inverting tube apparatus is shown in an undeployed stated, within an intermediate (e.g., delivery) catheter; the inversion support catheter includes an expandable funnel at the distal end over which a flexible tube inverts. The flexible tube is attached at a distal end region of the puller so that the puller may extend distally. In FIG. 3B the inverting tube apparatus of FIG. 3A is shown in a deployed configuration with at least the distal end extending from the intermediate catheter; the expandable funnel at the distal end of the inversion support catheter is in an expanded configuration.

FIG. 4B shows the inverting tube apparatus of FIG. 4A in a deployed configuration with the intermediate (e.g., delivery) catheter withdrawn proximally so that the expandable funnel at the distal end of the inversion support catheter can expand, and the flexible tube can expand.

FIG. 5A is a top perspective view and FIG. 5B is a side view.

FIG. 6A shows the expandable funnel in a collapsed form. FIG. 6B shows the expandable funnel deployed (e.g., from out of an intermediate or delivery catheter, not shown).

FIG. 6C shows the expandable funnel fully deployed by applying a compressive force along the long axis of the inversion support tube. FIG. 6D shows an example of an inverting tube apparatus including the inversion support catheter having an expandable funnel as shown in FIGS. 6A-6C.

In FIG. 7A, the inverting tube apparatus is shown next to a 4 mm clot prior to ingesting the clot.

FIG. 8A illustrate an example of an inverting tube apparatus in which the flexible tube inner diameter has been selected to match the outer diameter of the clot before the inverting tube apparatus has ingested the clot. FIG. 8B shows the clot after it has been captured (ingested) by the flexible tube of the inverting tube apparatus.

FIGS. 9A-9C illustrate the relationship between clot efficiency (e.g., the length of the flexible tube required to engulf and remove a clot), showing that the clot efficiency improves with larger outer diameter flexible tubes. FIG. 9A illustrates an example of an inverting tube apparatus engulfing a clot within a vessel. FIG. 9B is a graph showing the length of flexible tube (knitted flexible tube) required to ingest 5 cm of a clot having a 15 mm outer diameter (OD) into an inversion support catheter that is 8F (e.g., less than 2.67 mm) inner diameter (ID). FIG. 9C illustrates example of various inverting tube apparatuses having different flexible tube ODs.

FIG. 11A-11D illustrates an example of an inversion support catheter with an expandable funnel. FIG. 11A is a schematic illustration of an inversion support catheter including a funnel including a support frame that is formed from the distal end region of the elongate inversion support catheter. FIG. 11B shows an example of an inversion support catheter cut to form the supports shown schematically in FIG. 11A. FIG. 11C is an example of a distal funnel of an inversion support catheter formed by a braided material attached to a frame such as the frame shown in FIG. 11B. FIG. 11D is an end view of the funnel shown in FIG. 11C.

FIG. 13A is a schematic illustration of an inversion support catheter including a funnel including a support frame that is formed from the distal end region of the elongate inversion support catheter and a lubricious sleeve. FIG. 13B shows an example of an inversion support catheter such as the one shown schematically in FIG. 13A, including a lubricious sleeve. FIG. 13C is an example of a distal funnel of an inversion support catheter such as the one shown in FIG. 13B in an expended configuration. FIG. 13D is an end view of the funnel shown in FIG. 13C.

FIGS. 14A-14C illustrate examples of expandable funnels of inversion support catheters that may include lubricous sleeves within the mouth of the funnel to reduce the pulling force.

in FIG. 15A the fingers formed by cutting the distal end of the catheter are covered with a PTFE membrane in the mouth of the funnel.

FIG. 19 shows one example of a portion of the distal end of an inversion support catheter including a plurality of tines.

FIG. 20A is an example of a plurality of tines of an inversion support catheter having an expandable funnel that includes a filament connecting adjacent tines.

FIG. 20B is an enlarged view of the distal end of a tine (showing the filament) of FIG. 20A.

FIG. 22A is an example of an expandable funnel of an inversion support catheter in a relaxed state.

FIG. 22B shows the expandable funnel of FIG. 22A in a fully expanded configuration, with compressive stress applied.

FIG. 22C shows the expandable funnel of FIG. 22C collapsed and constrained in a loading sleeve.

FIG. 26 shows an example of a stop on a proximal end of an inversion support catheter, as well as an elastic cuff on a proximal end of the flexible tube of knitted or woven material.

FIG. 27A is an example of a lock configured to lock the inversion support catheter to a delivery catheter.

FIG. 27B illustrates the lock of FIG. 27A attached to both an inversion support catheter and a delivery catheter.

DETAILED DESCRIPTION

In general, described herein are inverting tube apparatuses (e.g., devices and systems) that are particularly well suited for removal of larger-diameter clots and/or atheromas. Any of the inverting tube apparatuses may include an inversion support catheter having an elongate and flexible body with an expandable funnel at a distal end of the body, and also a flexible tube that rolls and inverts over the inversion support catheter including the expandable funnel when the flexible tube is pulled proximally into the inversion support catheter. The inversion support catheters may be used with or without a flexible tube.

Figure 1A:
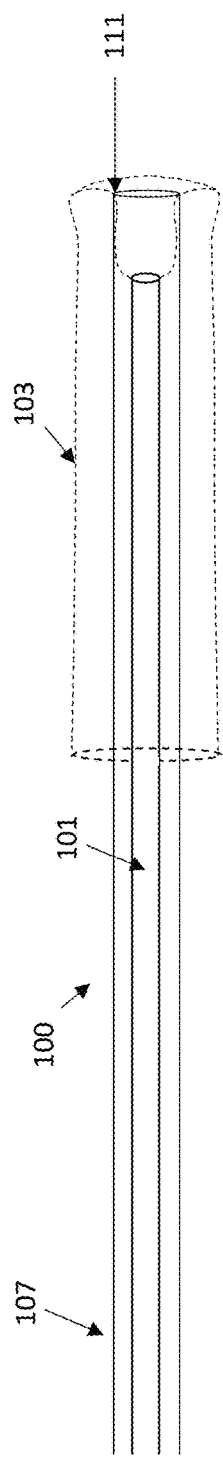
FIGS. 1A-1C illustrate an example of a mechanical inverting tube apparatus that is particularly well adapted for use in a small, and tortious vessel anatomy.
Figure 1B:
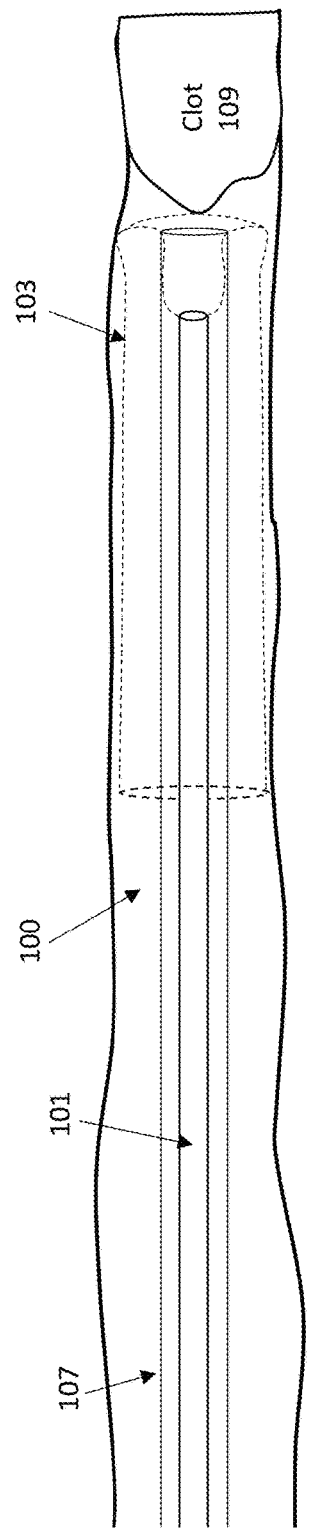
Figure 1C:
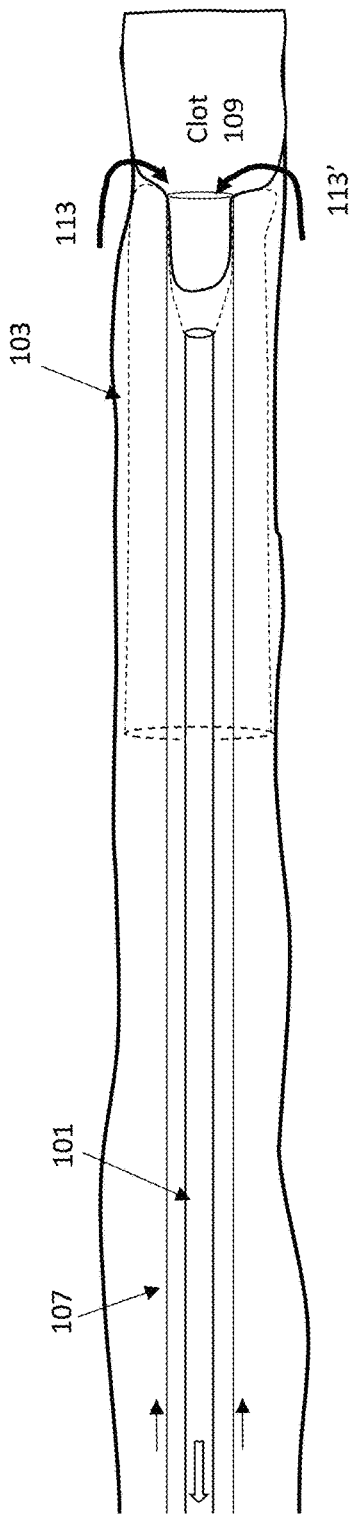

Previously described mechanical inverting tube apparatuses (also referred to as "mechanical thrombectomy apparatuses") were configured to remove clot effectively, as shown in FIGS. 1A-1C. The apparatuses and methods of using them described herein may particularly effective for use with the peripheral vasculature, including for use with relatively larger outer diameter clots (e.g., relative to the maximum inner diameter of the inversion support catheter into which the clot is pulled).

For example, FIG. 1A illustrates an example of an inverting tractor mechanical thrombectomy apparatus 100 (such as described in U.S. patent application Ser. No. 15/496,570, and U.S. patent application Ser. No. 15/043,996, each of which is herein incorporated by reference in its entirety).

In FIG. 1B the inverting tractor mechanical thrombectomy apparatus 100 is shown deployed near a clot 109. In the deployed configuration the puller 101 (shown here as a puller micro catheter, alternatively the puller may be a wire) is held within an elongate inversion support catheter 107 so that the flexile tractor tube 103 extends from the end of the puller 101 and expands toward the inner radius of the elongate inversion support catheter 107; at the distal end opening 111 of the elongate inversion support catheter the tractor tube inverts over itself and extends proximally in an inverted configuration over the distal end of the elongate inversion support catheter. As shown in FIG. 1C, by pulling the puller proximally, the tractor tube rolls 113, 113' and everts over the distal end opening of the elongate inversion support catheter, drawing the adjacent clot into the elongate inversion support catheter, as shown.

FIG. 1A the elongate inversion support catheter is an elongate tube having a distal end and that has the same size inner diameter as the proximal length of the inversion support catheter. The inversion support catheter 107 is shown positioned between the tractor tube (e.g., flexible tube 103) and the puller 101 so that the tractor tube can be pulled proximally by pulling on the puller and rolling the tractor tube into the elongate inversion support catheter so that it inverts. The portion of the tractor tube that is inverted over the distal end of the elongate inversion support catheter has an outer diameter that is greater than the outer diameter of the elongate inversion support catheter. The tractor may be biased so that it has a relaxed expanded configuration with a diameter that is greater than the outer diameter (OD) of the elongate inversion support catheter; in addition, the tractor tube may also be configured (e.g., by heat setting, etc.) so that when the tractor tube is everted and rolled over the distal end opening into the elongate inversion support catheter, the outer diameter of the tractor tube within the elongate inversion support catheter has an outer diameter that is about y times the inner diameter of the elongate inversion support catheter (e.g., where y is greater than 0.1×, 0.5×0.6×, 0.7×, 0.75×, 0.8×, 0.9×, 1×, etc. the inner diameter, ID, of the elongate inversion support catheter. This combination of an un-inverted diameter of the tractor tube of greater than the diameter of the OD of the elongate inversion support catheter and an inverted diameter of the tractor tube of greater than, e.g., 0.7× the ID of the elongate inversion support catheter is surprisingly helpful for preventing jamming of the apparatus, both when deploying the apparatus and when rolling the tractor over the distal end opening of the elongate inversion support catheter to grab a clot. The tractor may be expandable and may be coupled to the puller as shown. In some variations the flexible tractor and the puller may comprise the same material but the tractor may be more flexible and/or expandable, or may be connected to elongate puller (e.g., a push/pull wire or catheter).

In FIG. 1C the clot may be drawn into the elongate inversion support catheter by pulling the tractor proximally into the distal end of the elongate inversion support catheter, as indicated by the arrows 113, 113' showing pulling of the inner portion of the flexible tractor, resulting in rolling the tractor over the end opening of the catheter and into the catheter distal end and inverting the expandable distal end region so that it is pulled into the catheter, shown by arrows.

The end of the tractor outside of the catheter may be "loose" relative to the outer wall of the catheter.

Figure 2:
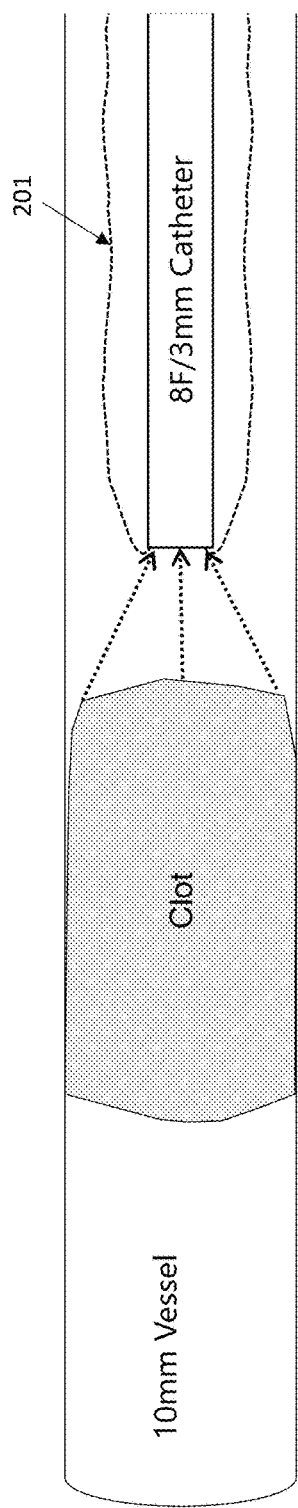
FIG. 2 is an example of an inverting tube apparatus similar the one shown in in FIG. 1A in a large vessel, having clot with a diameter that is greater than 2× the inner diameter of the inversion support catheter. Although the clot may be ingested and removed by the inverting tube apparatus having a narrower-diameter inversion support catheter, the efficiency of the inversion may be low, e.g., requiring a flexible tube having approximately 12× the length of the clot tube to capture the entire clot.

FIG. 2 illustrate an example of an inverting tube apparatus 201 similar the one shown in in FIG. 1A. In this example, the inverting tube apparatus is in a large vessel that has a clot with a diameter that is greater than 2× the inner diameter of the inversion support catheter. Although the clot may be ingested and removed by the inverting tube apparatus 201 having a narrower-diameter inversion support catheter, the efficiency of the inversion may be low, e.g., requiring a flexible tube having approximately 12× the length of the clot tube to capture the entire clot. This figure illustrates the problem addressed by the apparatuses described herein; specifically, how to efficiently ingest long and large diameters clots (e.g., greater than 10 mm) into relatively smaller diameter inverting tube apparatuses. In this example, while the 10 mm or larger diameter clot may be pulled into a 3 mm diameter (e.g., 8 French) inversion support catheter of the inverting tube apparatus, the efficiency is low, because the length of the flexible tube that must be used to capture the entire length of the clot is extremely high. Specifically, a 1 cm long clot having a diameter of 10 mm would require 12 cm of flexible tube when inverted and pulled into a 3 mm catheter; thus a clot that is 5 cm long would require 60 cm of flexible tube. The inverting tube apparatuses described herein may address and improve this efficiency in a number of ways.

In particular, the methods and inverting tube apparatuses described herein may dehydrate the clot as it is drawn into the inverting tube apparatus. Clots, including even hard or partially calcified clots, may include a large amount of fluid that may be compressed and removed by the inverting tube apparatuses described herein. For example the flexible tube is typically porous, and may be, for example, a knitted material. In addition, in some variations the distal end region of the inversion support tube may be configured, particularly at the distal end region (e.g., the distal 5 mm, distal 4 mm, distal 3 mm, distal 2 mm, distal 1 mm, distal 0.9 mm, distal 0.8 mm, distal 0.75 mm, distal 0.7 mm, distal 0.6 mm, distal 0.5 mm, distal 0.4 mm, etc.) may be porous to allow fluid to escape laterally out of the inversion support catheter from the clot as the clot is drawn into the elongate inversion support catheter, so that the cot may compress more efficiently, rather than elongate or stretching. In particular, described herein are apparatuses and methods that include a funnel-shaped distal end on the inversion support catheter that may be porous (particularly at the region near the base of the funnel) to allow compression of the clot material and ejection/removal of fluid from the clot laterally out of the sides of the inversion support catheter as clot is drawn proximally into the inversion support catheter by the rolling of the flexible tube (e.g., tractor). The funnel may be expandable (also referred to herein as collapsible) and may be integral with or attached to the distal end of the inversion support catheter. The funnel may be collapsed and introduced through a sheath/guide catheter (e.g., an intermediate catheter), so that it may fit, in a collapsed state, into a 6 French, 8 French, 10 French, 12 French, 14 French, 16 French, 28 French, 20 French, and/or 24 French sheath. The expandable funnel may be self-expanding. Alternatively or additionally, the expandable funnel at the distal end of the inversion support catheter may be expanded by actuation of the flexile tube; e.g., pulling the flexible tube into the inversion support catheter proximally to roll the flexible tube over the distal end of the inversion support catheter may apply a proximally-directed compressive force that pulls and expands the expandable funnel. The funnel may have a maximum outer diameter that is greater than 2× (e.g., greater than 2.5×, greater than 3×, greater than 3.5× greater than 4×, greater than 4.5×, greater than 5×, etc.) the maximum outer diameter of the collapsed configuration; the maximum outer diameter of the funnel in the collapsed configuration may be approximately the same as, or slightly larger than, the maximum outer diameter of the body region of the inversion support catheter (e.g., 1×, 1.01×, 1.1×, 1.2×, etc. the outer diameter of the proximal portion of the inversion support catheter). In some variations the funnel has an outer diameter of between 2-26 mm.

In any of these variations, the flexible tube may also be adapted to better engulf and compress large-diameter clots. For example the flexile tube in the un-inverted configuration when outside of the inversion support catheter (e.g., in the vessel) may have an outer diameter that is selected to be approximately the same as or larger than the maximum outer diameter of the expanded configuration of the funnel.

The of an expandable funnel may allow the flexible tube (e.g., woven tractor) to grab clot at edges of cross section rather than the center of clot, which may enable a more efficient clot ingestion.

In flexible tube variations (e.g., tractor variations) described herein, it may be beneficial to have the expanded non-inverted outer diameter of the flexible tube (e.g., the portion of the flexible tube on the outside of the inversion support catheter prior to being pulled into the catheter and inverted) be heat-set to a larger diameter (OD) than the maximum outer diameter of the expanded funnel, and preferably as large as possible with respect to the clot OD. Larger OD flexible tube may have higher efficiency for grabbing and compressing clot. This may be independent of whether there is a funnel on the distal end of the inversion support catheter. For example, for a flexible tube (e.g., tractor) formed of a woven material, the OD of the un-inverted flexible tube may be selected to be at least ⅓rd of the clot OD (or vessel ID), for example, the expanded, un-inverted flexible tube may have an OD that is greater than or equal to about 50%, 60%, 70%, 80%, 90%, 100% or 110% of the clot OD (or vessel ID).

As already discussed, the distal end of the inversion support catheter, and particular an expandable funnel on the distal end, may be porous. The ability to allow fluid from compressed clot to exit from out of the sidewalls of the funnel inner diameter (e.g., lateral to the walls of the inversion support catheter, rather than just from the distal and proximal ends) may provide a place for the fluid removed from the clot to go and may improve the efficiency of the apparatus, allowing for much shorter flexible tubes to remove a comparable length of clot. If the clot is not allowed to escape laterally (e.g., when using a non-porous funnel), the fluid removed may build up at the base of the funnel and may reduce the clot efficiency. Thus, in some variations, the funnel is porous or at least partially porous, e.g., near the base of the funnel, where the compressive ratios of the clot are the highest.

In any of the variations described herein, the inversion support catheter may be relatively large, so that the clot does not have to be compressed as much. In the peripheral vasculature, for example, the inversion support catheter may have an outer diameter that is greater than 1 mm, e.g., greater than 1 mm, 1.2 mm, 1.4 mm, 1.5 mm, 2 mm, 2.5 mm, 3 mm, 3.5 mm, 4 mm, 4.5 mm, 5 mm, etc.

In general, any of the apparatuses described herein may also increase the efficiency of the apparatus for removing clot by reducing the force need to remove the clot. For example, the methods and apparatuses described herein may include a lubricious material on the distal end (e.g., the funnel) of the inversion support catheter. For example, in any of these apparatuses the funnel may be lined with a slippery material (e.g., a PTFE liner) that may produce a lower ingestion pull force and/or may reduce the ingesting efficiency. Slippery funnels may allow a clot mass to be drawn into the mouth of funnel rather than pulling it into the catheter.

In some variations the funnel may be configured to have a specific shape (e.g., taper) that may also assist in increasing the efficiency for compressing and/or dehydrating the clot and may help reduce the amount of force required. For example, in some variations, longer funnels may have a lower ingesting forces and better clot ingesting efficiency compared to shorter funnels of the same maximum OD/minimum ID. Examples of funnels may have a maximum OD of, e.g., 3 mm, 5 mm, 6 mm, 8 mm, 10 mm, 12 mm, 15 mm, 20 mm, 25 mm, etc. Exemplary funnel lengths may be, for example, 5 cm, 10 cm, 15 cm, 20 cm, 25 cm, 30 cm, 40 cm, 50 cm, 50 cm, 100 cm, etc. The body portion of the elongate flexible inversion catheter may be, e.g., a 3 French (F), 4 F, 5 F, 6 F, 7 F, 8 F, 9 F, 10 F, 11 F, 12 F, 14 F, 16 F, 18 F, 20 F, 25 F, etc. catheter.

For variations in which the flexible tube comprises a woven material, coarser waves may have increased efficiency. For example, a larger number of weave "fingers" (e.g., loops) in the transverse direction of the tube may (per weave circumference) may have a greater clot ingesting efficiency. For example, the number of grabbing fingers may be at least 10, 20, 20, 40, 50, 60, 100, etc., per tubular weave circumference.

In general the inverting tube apparatuses described herein may be highly flexible, both before actuating and during operation. For example, the flexible tube (e.g., tractor) may not significantly increase the stiffness/flexibility of the catheter of the elongate inversion support, and particularly the distal end region of the catheter, to avoid impacting maneuverability. Described herein are flexible tractor tube portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tractor tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

The flexible tube (e.g., tractors) may be woven, braided and/or knitted materials. For woven and braided materials, which may include a plurality of fibers that are woven or braided to form the inverting tube, these structures may be tuned to prevent jamming and/or to reduce the force necessary to pull the tractor and invert over the catheter tip. For example, the mechanical atherectomy apparatus may include a knitted or braided flexible tubes that can roll freely around the tip of catheter even in a tortuous anatomy and when grabbing clot by tuning one or more of the braid structure; minimizing the braid angle; including a hydrophilic coating on the distal aspect of the catheter outer diameter (OD) or the inner diameter (ID) of the braid (e.g., tractor); including a radiused wall on the catheter; and/or increasing the stiffness of the distal tip region relative to adjacent proximal regions. Alternatively it may be advantages to have a hydrophilic coating on 1, 3, 5, 10, or 15 cm of the distal ID or the entire catheter ID.

As mentioned, the flexible tube (e.g., tractor) may be braided, woven, knitted, etc., and may be configured to collapse down into the inner diameter (ID) of the catheter as little as possible. For example the tractor may collapse to an ID that is greater than, equal to, or within 90%, 85%, 75%, 70%, 65%, 60%, or 50% of the catheter inner diameter (ID)/Catheter Tip OD, since, where this ID is based on the elongate body region of the inversion support catheter, when the tractor is being pulled around catheter tip it may create axial tension on the tractor (e.g., braid, knit, etc.) that may otherwise inadvertently and undesirably cause the tractor to jam on the catheter tip. When tractor is pulled around catheter tip, the tractor may be pulled in the axial orientation creating axial tension on tractor structure as the tractor is being pulled through the catheter ID. By having the tractor elements jam at an ID greater than or equal to 90%, 85%, 75%, 70%, 65%, 60%, or 50% of the catheter ID (or in some variations, OD), when being axially tensioned, the tractor is less likely to grab/synch down onto the catheter tip, helping the braid roll around the catheter tip with less axial force applied by the user. If less axial force is required by the user to pull the tractor structure around the tip then the catheter tip is less likely to buckle or deflect when retracting the tractor. It may be advantageous to minimize the chance the catheter tip will buckle. The tractor can be tuned to "jam" at a specific ID by controlling any of the following variables and in any combination: selecting a specific number of braid ends, selecting the size/diameter of the braid ends; selecting the braid material (e.g., multifilament or monofilament); heat setting the bias on the braid (e.g., braid diameter); and selecting a braid pattern, e.g., 1×2, 1×1 or any other pattern.

The braid angle may be minimized to prevent locking up of the rolling of the tractor over the catheter end opening. Typically, the lower the braid angle (e.g., 45 degrees or less, 40 degrees or less, 35 degrees or less, 30 degrees or less, 25 degrees or less, 20 degrees or less, etc.) the less likely it is to have the braid cross over points catch on the catheter tip.

In any of the variations described herein, the catheter and/or a surface of the tractor may be coated to enhance rolling over the distal end region of the catheter. It may be helpful to have a hydrophilic coating on the distal aspect of the catheter OD or the ID of the tractor so the tractor can more easily side over the catheters distal end and around the tip of the catheter when pulled through the inside of the catheter.

The stiffness of the distal of the elongate inversion support catheter may be sufficiently stiff to prevent collapse as the tractor is pulled; it may also be lubricious (e.g., by a coating or material property). The distal most section of the elongate inversion support catheter tip (e.g., the last 5 mm) may be fabricated of a material which is stiff enough and lubricious enough so the distal tip of the catheter does not collapse or buckle inward ward when the braid structure is rolling around the catheter tip. Thus, the distal tip may have a stiffness that is greater than the more proximal region at the distal end of the catheter.

Figure 3A:
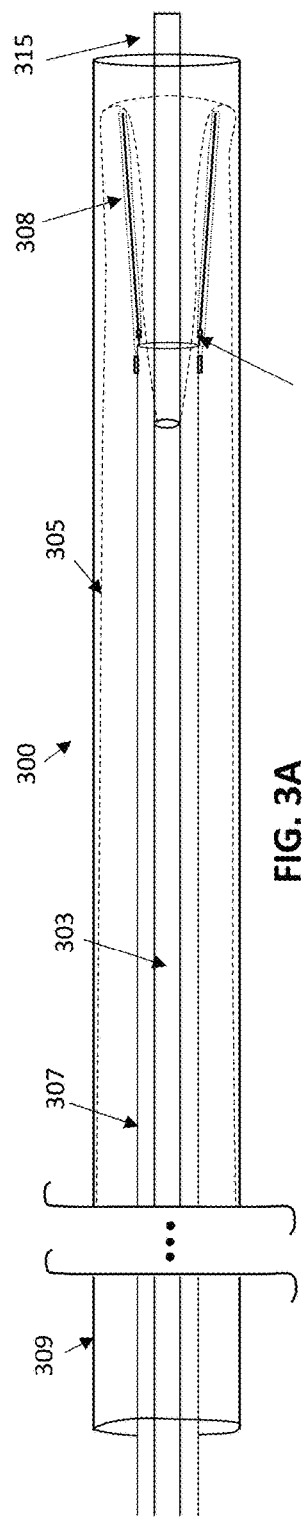
FIGS. 3A-3B shows an example of an inverting tube apparatus adapted to dehydrate (e.g. remove liquid) from the clot as it is ingested, increasing the efficiency of the inversion.
Figure 3B:
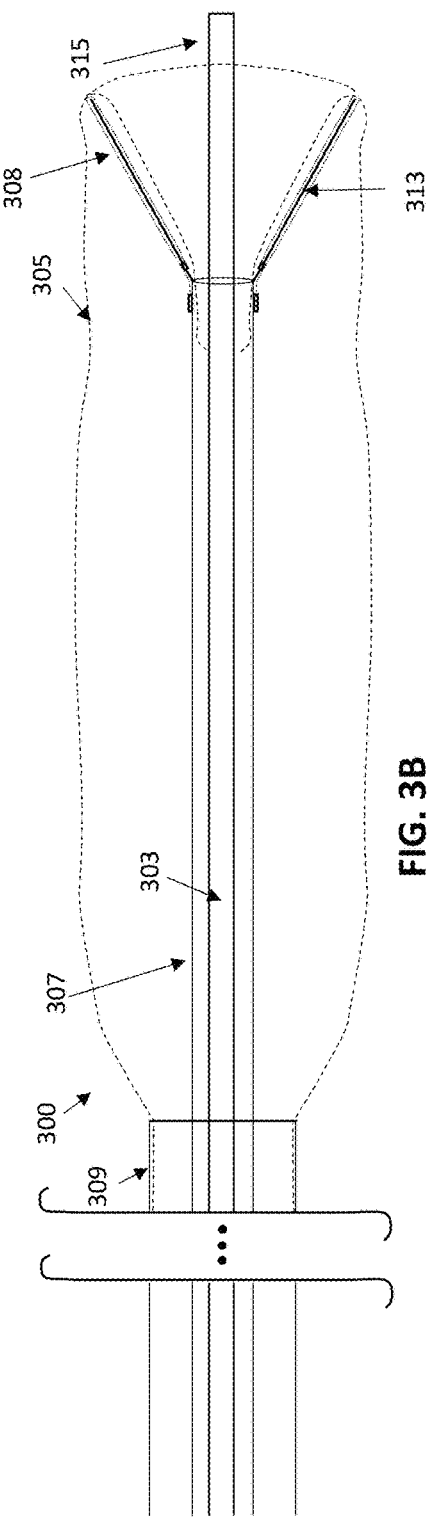

FIGS. 3A-3B and 4A-4B illustrate examples of inverting tube apparatuses that each include a funnel region at the distal end of an inversion support catheter. For example, FIG. 3A shows a first variations of an inverting tube apparatus 300 that includes an elongate, flexible inversion support catheter 307 that has an expandable funnel 308 at the distal end, shown in a collapsed configuration in FIG. 3A within an intermediate (e.g., delivery) catheter 309, and in an expanded configuration in FIG. 3B after being released from the intermediate catheter. The funnel may be formed of a woven material and may be porous, particularly at the base region 313, where the funnel extend from the body of the elongate body of the inversion support catheter. A flexible tube 305 extends over the distal end (including the funnel) of the inversion support catheter and inverts over the distal opening of the funnel. The flexible tube may be, e.g., a knitted material, and may be biased to expand to an outer diameter (OD) that is larger than the OD of the funnel 308 in the expanded configuration. The flexible tube is attached to a distal end region of a puller 303. In the example shown in FIGS. 3A-3B the puller extends distally 315 further than the distal end of the funnel, as shown. Although the flexible tube (e.g., tractor) is attached to the distal end region of the puller, the end of the flexible tube in this example is attached proximally of the distal end of the device.

Figure 4A:
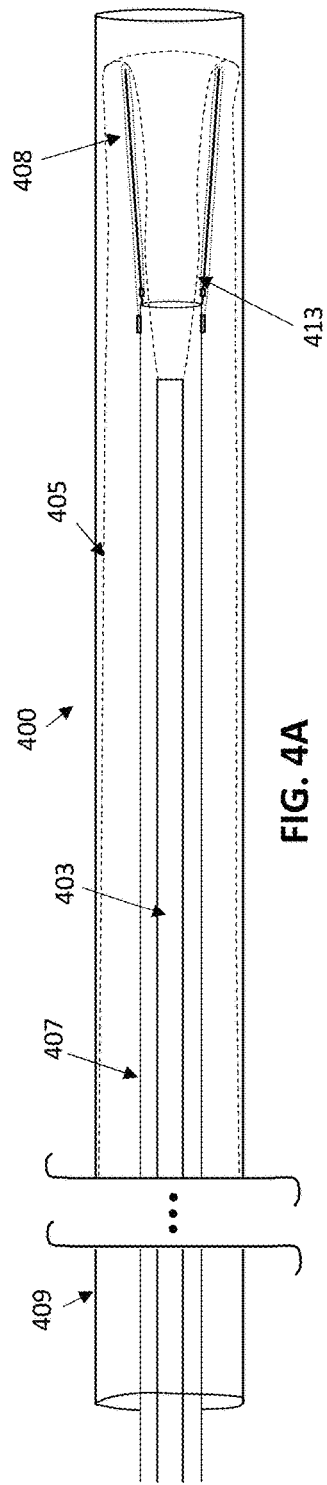
FIGS. 4A-4B illustrate another example of an inverting tube apparatus including an expandable funnel, in which the flexible tube (e.g., knitted tube) is attached to distal end of a puller.
Figure 4B:
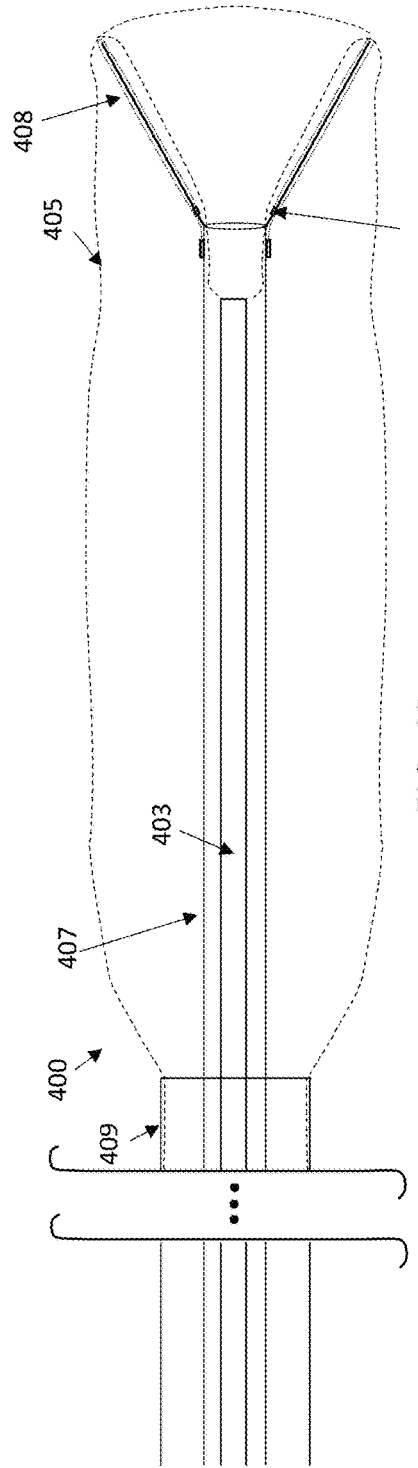

In the example of an inverting tube apparatus 400 shown in FIGS. 4A-4B, the flexible tube 405 is attached at the distal end region of the puller 403 closer to or at the distal end of the puller. FIG. 3A shows the inverting tube apparatus 400 within an intermediate catheter (e.g., deliver catheter) 409 with a funnel 408 at the distal end of the inversion support catheter 407 within the intermediate catheter in a collapsed configuration. The funnel may include one or more (e.g., a plurality of circumferentially-arranged) openings or pores at the base 413 region to permit fluid from the clot to exit the inversion support catheter as the clot is pulled into the inversion support catheter by the rolling flexible tube 405 (e.g., tractor region). FIG. 4B shows the apparatus at least partially deployed from out of the intermediate catheter 409, with the expandable funnel 408 expanded.

Figure 4C:
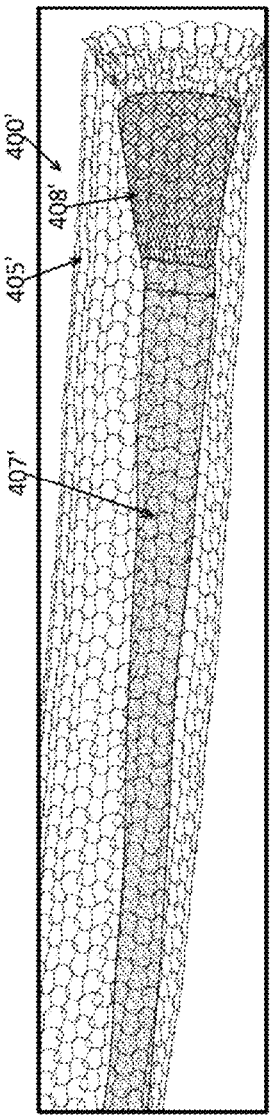
FIG. 4C is an image of a prototype of an inverting tube apparatus similar to that shown in FIGS. 4A-4C.

FIG. 4C is a picture of a prototype apparatus 400' in which the inversion support catheter 407' includes an expandable funnel 408' (shown expanded) and over which a flexible tube 405' may roll and invert to capture clot material when used as a thrombectomy device. In FIG. 4C the flexible tube is shown as a knitted tube, forming a plurality (e.g., >15) of loops or fingers at the distal-facing end of the apparatus, which may help capture clot material. This is shown in more detail in FIGS. 5A and 5B.

Figure 5B:
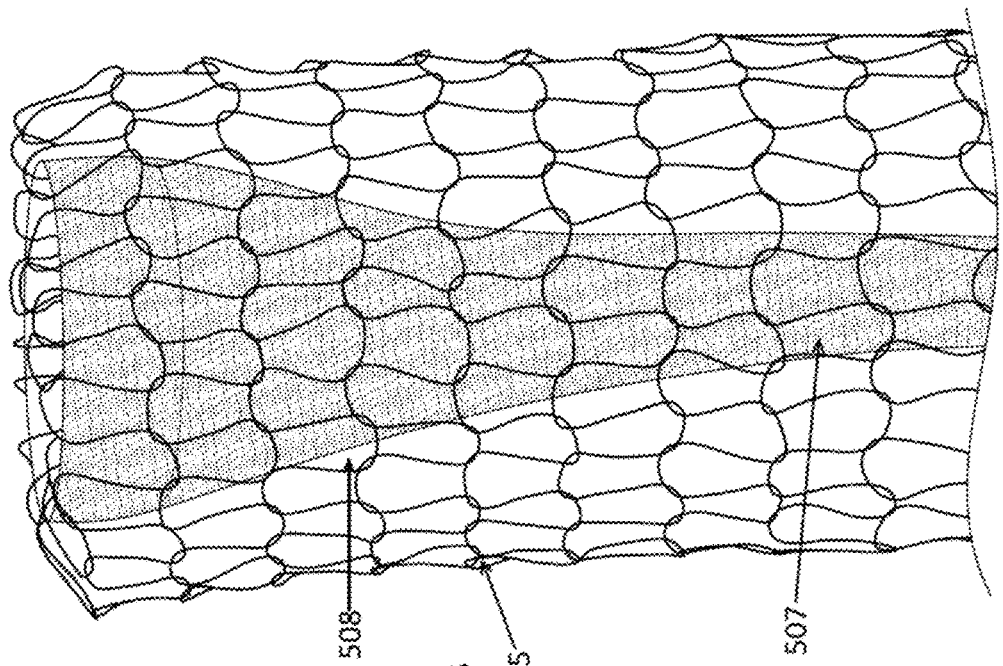
FIGS. 5A-5B show an example of the distal end of an inverting tube apparatus including a funnel at the distal end of the inversion support catheter, over which the knitted flexible tube rolls and inverts.
Figure 5A:
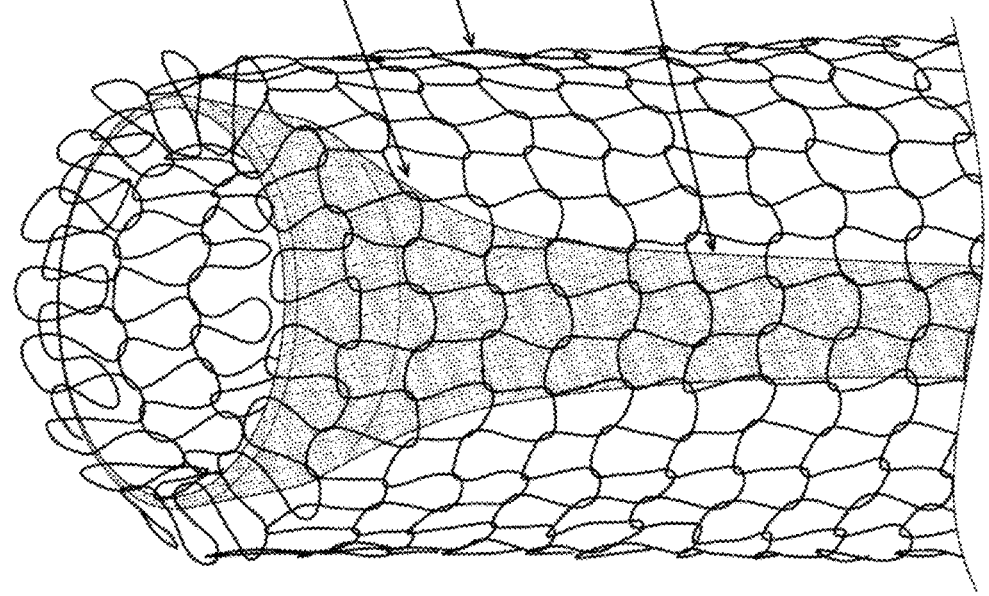

In FIGS. 5A and 5B, a porous funnel 508 forming the distal end of an inversion support catheter 507 is shown with a knitted flexible tube 505 shown inverting over and into the funnel when the flexible tube is pulled proximally into the funnel.

Figure 6C:
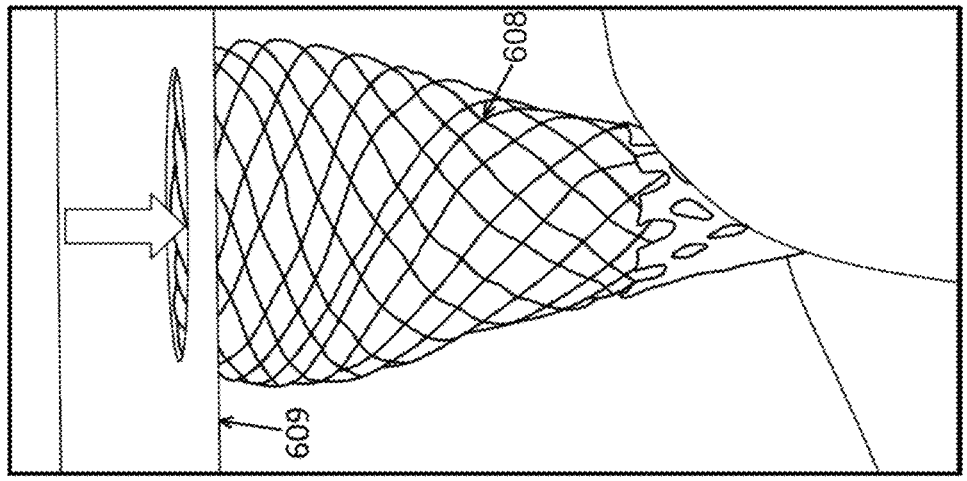
FIGS. 6A-6D illustrate one example of a prototype inversion support catheter including an expandable funnel at the distal end, which may be used with an inverting tube apparatus.
Figure 6B:
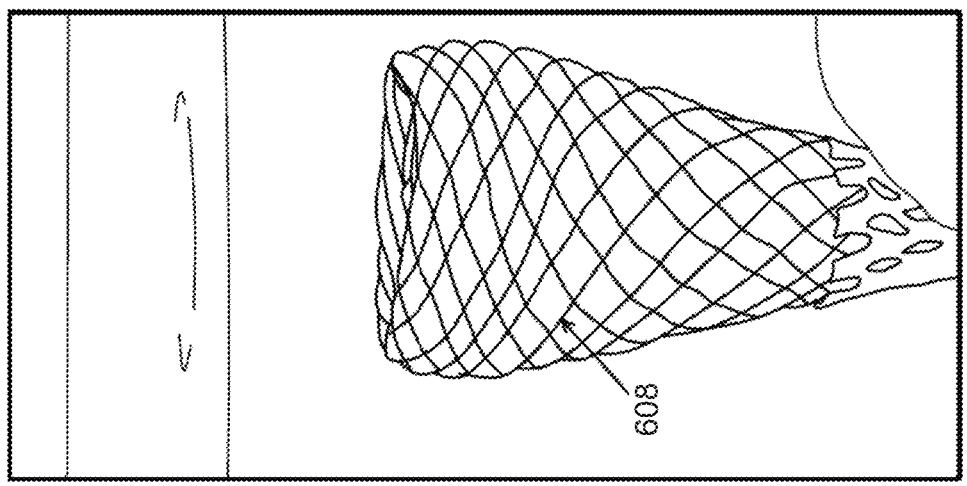
Figure 6A:
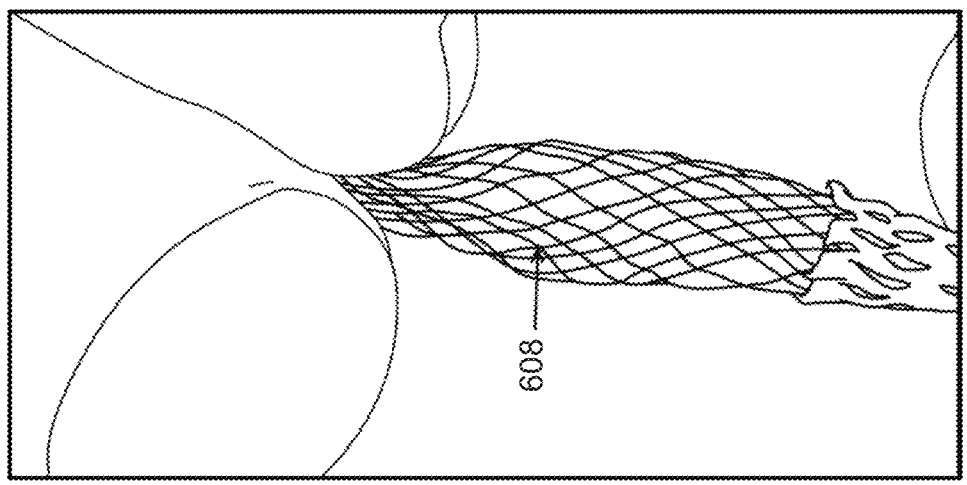
Figure 6D:
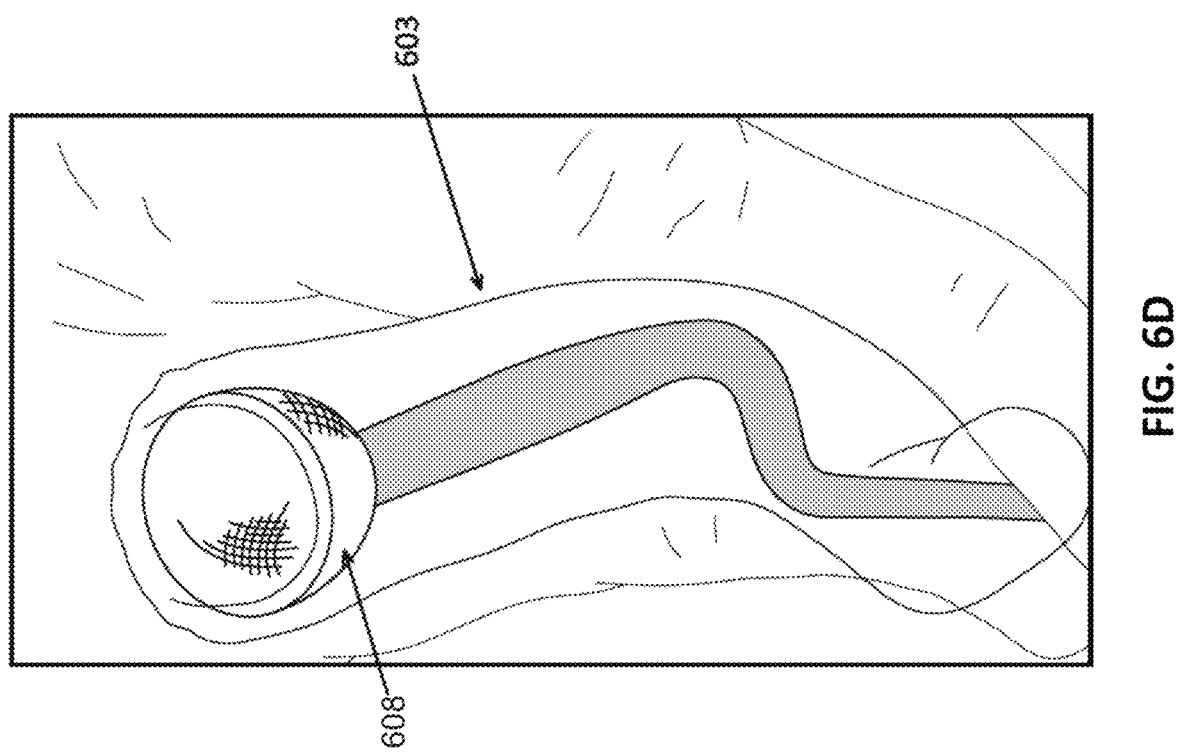

In some variations the expandable funnel may be formed of a woven and/or braided material, as shown in FIGS. 6A-6D. For example in FIG. 6A the funnel is configured to handle a relatively large compressive load as may be necessary to compress and/or dehydrate a large-diameter clot when drawing the clot into the device. In FIG. 6A the funnel 608 is shown collapsed; the funnel can collapse to a smaller OD to enable introduction through small ID sheath, for example by elongating the funnel shape, as shown. The funnel may be self-expanded, as shown in FIG. 6B to a fully or partially expanded configuration, e.g., when released from a delivery catheter within the vessel. In some variation the funnel may further expanded (more fully) when pressed into a clot or against a body 609, as shown in FIG. 6C, resulting in a compressive force 611 being applied in the proximal direction on the funnel, jamming it into a higher-strength configuration, as will be shown in greater detail in FIG. 12, below. FIG. 6D shows a distal perspective view of a funnel end of an inversion support catheter with a knitted tractor (knitted flexible tube) 603 inverting into the funnel. In this example, the funnel flares outward from a 5 mm ID to an 8 mm ID in the expanded configuration.

Figure 7A:
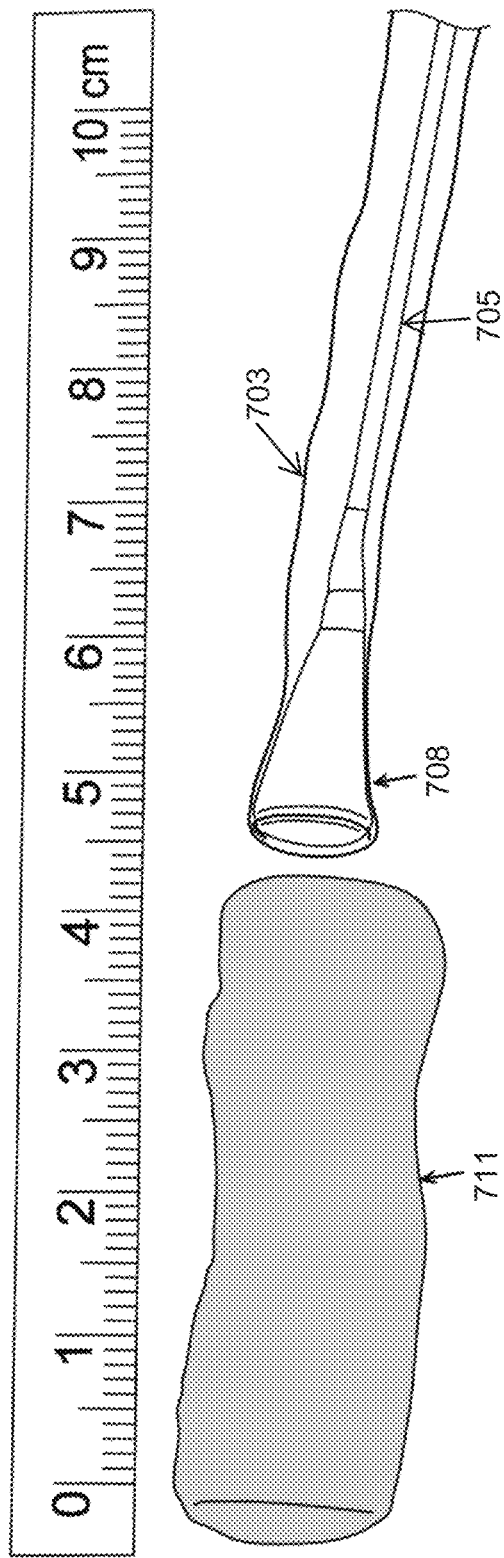
FIG. 7A illustrates one example of an inverting tube apparatus configured to dehydrate a clot as it engulfs the clot.
Figure 7B:
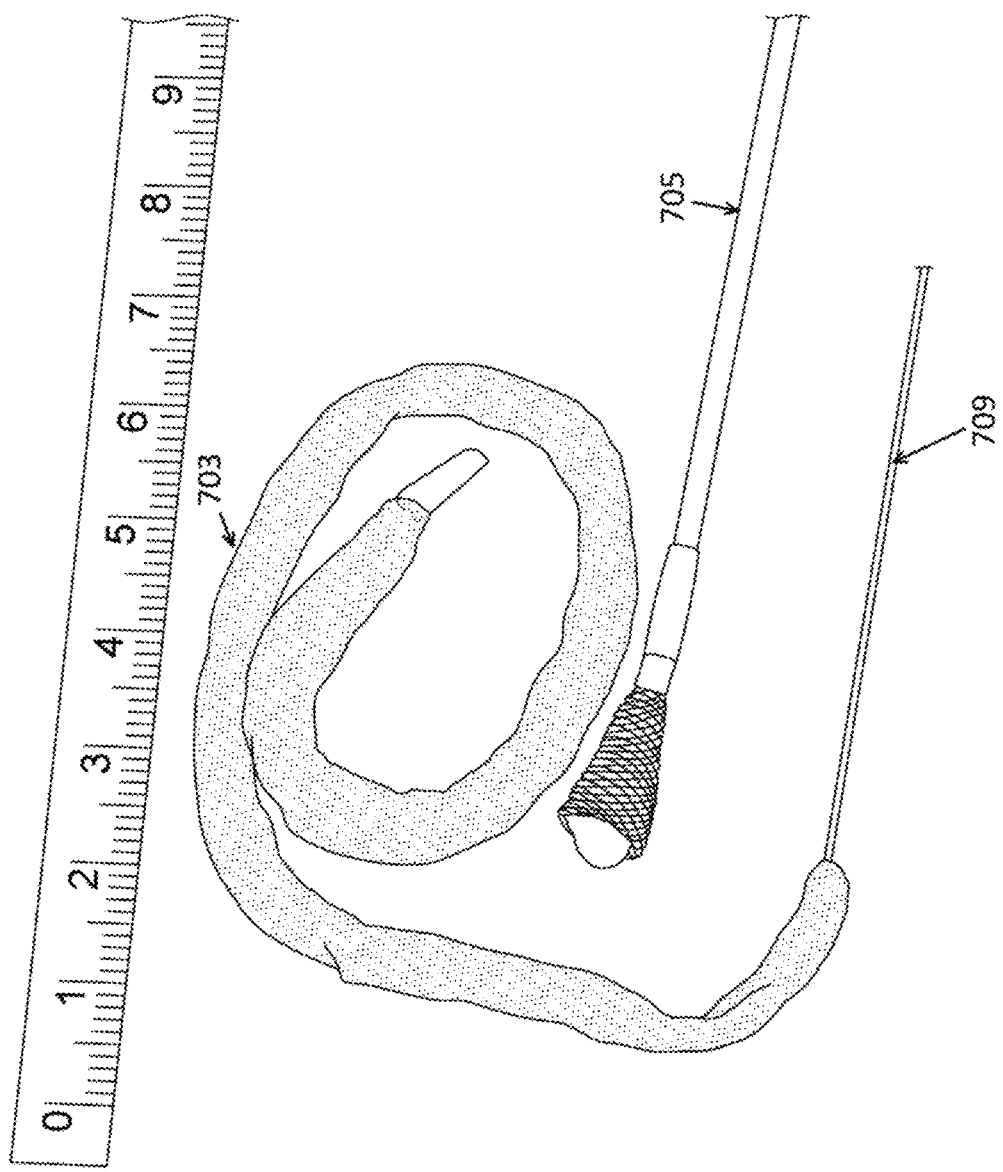
FIG. 7B shows the inverting tube apparatus after it has engulfed the clot, with the flexible tube removed from the inversion support catheter having an expandable funnel.

FIGS. 7A and 7B illustrate an example of an inverting tube apparatus with a flexible tube (e.g., knitted tractor tube 703) and an inversion support tube 705 including an expandable funnel 708 ingesting a clot 711. FIG. 7A shows the clot and apparatus before ingesting. FIG. 7B shows the clot within the flexible tube after ingestion into the inversion support catheter, after the flexible tube has been removed from within the inversion support tube (the woven flexible tube is shown attached to a puller 709). Similarly, FIGS. 8A-8B illustrates another example of an inverting tube apparatus 800, shown with a non-funnel tipped inversion support catheter 807 has been heat set so that the woven flexible tube (tractor tube) has an outer diameter approximately equal to the OD of the clot 811, resulting in a relatively high clot efficiency, as shown in FIG. 8B, showing the captured clot 811' after removal from the apparatus.

As illustrated in FIGS. 9A-8C, in general, the clot removal efficiency may increase with the size of the outer diameter of the flexible tube. FIG. 9A shows an example of an inverting tube apparatus (thrombecomy apparatus) 900 that includes an inversion support catheter 907 and a woven flexible tube 905. FIG. 9B is a graph showing the length (in cm) of the knitted flexible tube (tractor tube) of the apparatus needed do fully capture a 5 cm length of clot having an outer diameter of 15 mm. As shown the larger the outer diameter of the flexible tube in the un-inverted, expanded configuration, e.g., on the outside of the inversion support catheter, the smaller the length of knitted flexible tube needed. FIG. 9C illustrates examples of various inverting tube apparatuses, showing exemplary dimensions.

Figure 10B:
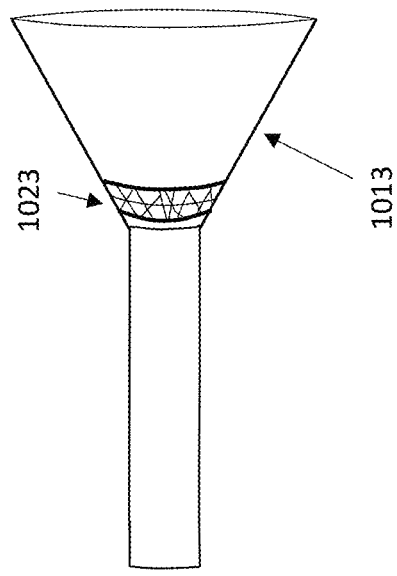
FIGS. 10A-10D illustrate examples of inversion support catheters with expandable funnels at their distal ends.
Figure 10D:
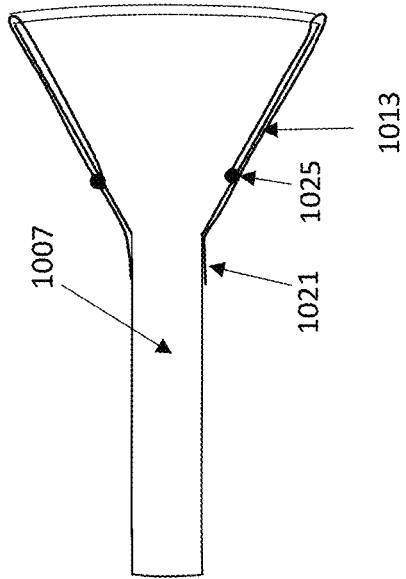
Figure 10A:
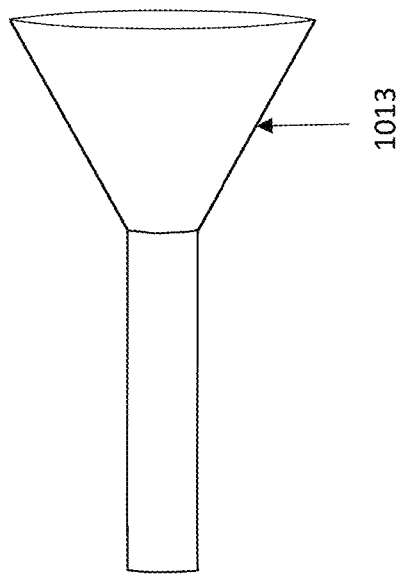
Figure 10C:
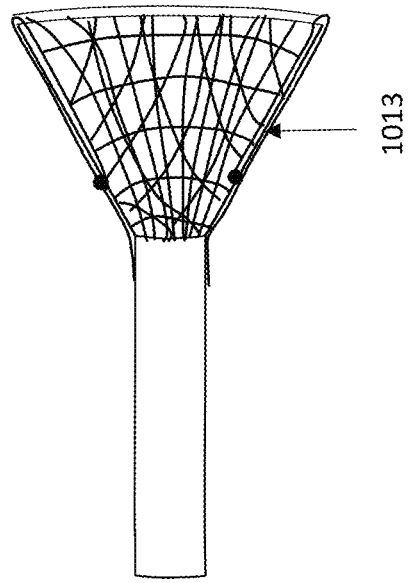

Any appropriate expandable funnel-shaped distal ends may be used. For example, FIGS. 10A-10C illustrate different variations of funnel-shaped distal ends. In FIG. 3A the funnel 1013 is shown and may be solid or may include openings for allowing the passage of fluid (e.g., may be porous), including porous over its entire surface. FIG. 10B shows an example in which only a portion of the expandable funnel is porous. In FIG. 10B, the base region 1023 is porous, and includes a plurality of openings arranged circumferentially around the perimeter of the base region of the funnel 1013.

The expandable funnel 1013 variation shown in FIG. 10C is porous over its entire length, and is shown formed of a woven material (e.g., a metal or polymeric fiber) that may be doubled back over itself to form the funnel-shape. FIG. 10D shows a cross-section through the variation of FIG. 10C, showing attachment 1021 of the tubular weave forming the funnel to the outside of the body region of the elongate, flexible inversion support catheter 1007 and at a second end 1025 of a portion of the funnel within the mouth of the funnel. Any of these variations may include a lubricious sleeve (e.g., a Teflon sleeve).

FIGS. 11A-11D illustrate one example of a distal end of an inversion support catheter including a funnel. In this example, the funnel is formed integrally with the body of the inversion support catheter. As shown by the schematic in FIG. 11A, the funnel shape includes a framework formed by a plurality of fingers or struts 1111 formed by cutting (e.g. laser cutting) the distal end of the body of the inversion support catheter 1107. In FIG. 11A a braided or woven funnel body 1118 is attached to the struts; the woven body is attached 1105 to the body of the inversion support catheter on one end, and on the other end 1109 to lock it in place over the struts. FIG. 11B shows an example of a body of an elongate support catheter that has been cut into a plurality of struts or fingers over which the funnel body may be supported, as shown in FIG. 11C. The distal end of the funnel 1131 is opened and may extend beyond the struts and may jam to form a locked open configuration having a high compression strength, even in the absence of the underlying struts or fingers. FIG. 11D shows an example of an open distal end of the funnel of the apparatus.

Figure 12:
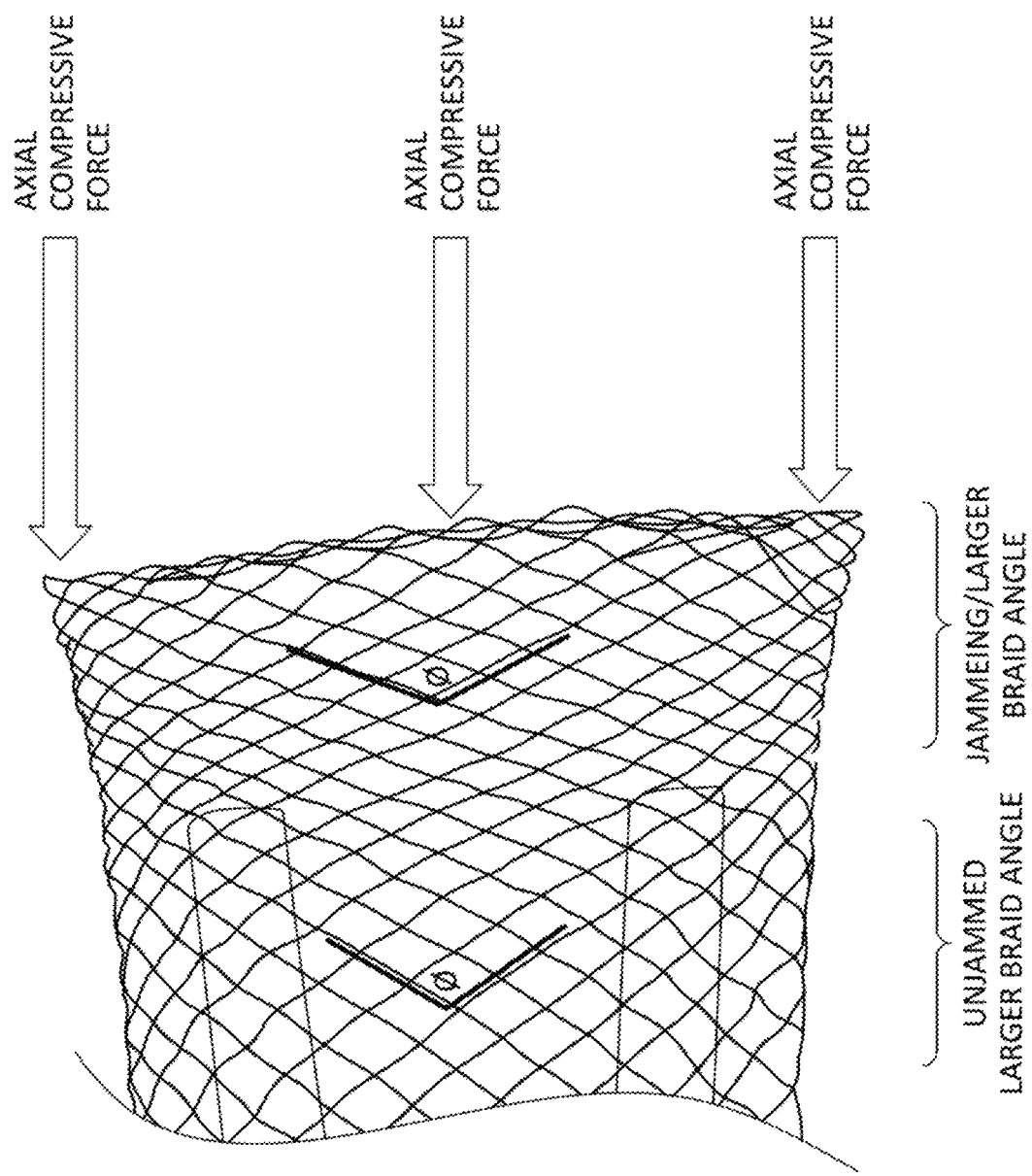
FIG. 12 is an example of a funnel of an inversion support catheter that is configured to have an axial compressive strength that is sufficient to resist collapsing when greater than 500 g (e.g., greater than 1 kg, greater than 1.2 kg, greater than 1.5 kg, etc.) of axial compressive force is applied. In this example, the axial compressive force, which may be applied by the flexible tube being drawn proximally (e.g., pulled) to roll over the distal end of the funnel, may also open the funnel to deploy it.

FIG. 12 is an enlarged version of the distal end of the funnel shown in FIG. 11C, illustrating the application of axial compression that may cause the distal end of the apparatus to 'jam' and from a larger braid angle (θ) at the distal end, compared to the unjammed more proximal end. This compressive force may help open (and hold open) the expandable funnel.

Figure 13C:
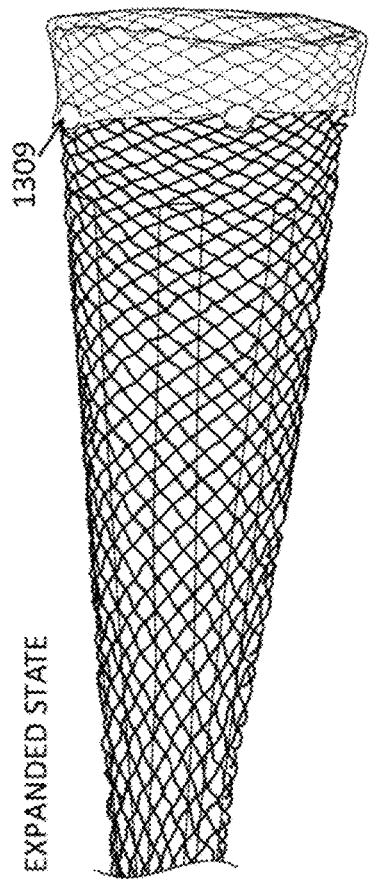
FIGS. 13A-13D illustrates an example of an inversion support catheter with an expandable funnel that is lined with a lubricious (e.g., Teflon) sleeve.
Figure 13D:
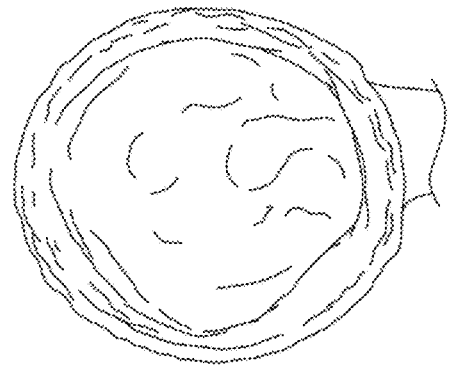
Figure 13A:
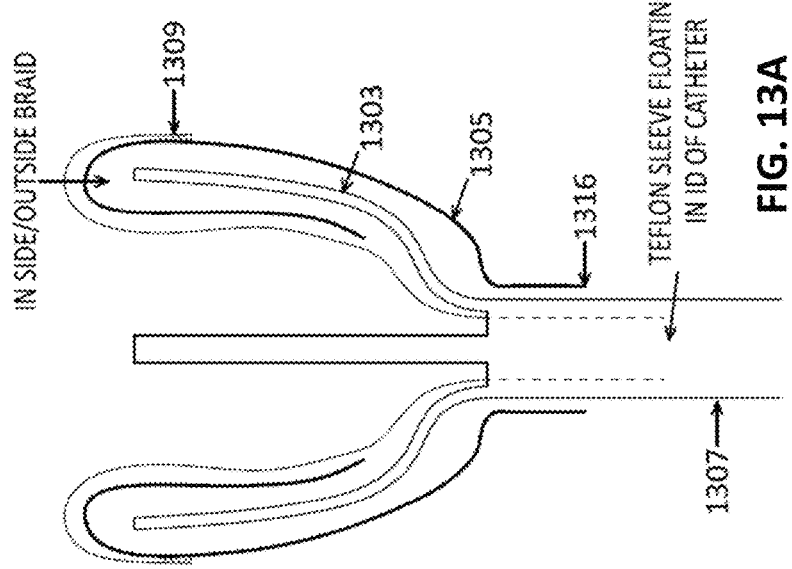

FIGS. 13A-13D show another variations of a funnel portion of an inversion support catheter, including a lubricious sleeve (e.g. Teflon sleeve). In FIG. 13A, a schematic of the funnel shows that it may be formed of a plurality of arms 1303 and a braided funnel body 1305 may be bonded over the arms (similar to the variation shown in FIGS. 11A-11D) formed from the body of the inversion support catheter 1307. The braided body may be bonded to the catheter body 1316. In addition, a Teflon sleeve 1309 may be attached at one or more locations along the OD of the braided body region, as shown. In FIG. 13A, the Teflon sleeve does not cover the base region, allowing fluid to exit the funnel laterally near the base of the funnel.

Figure 13B:
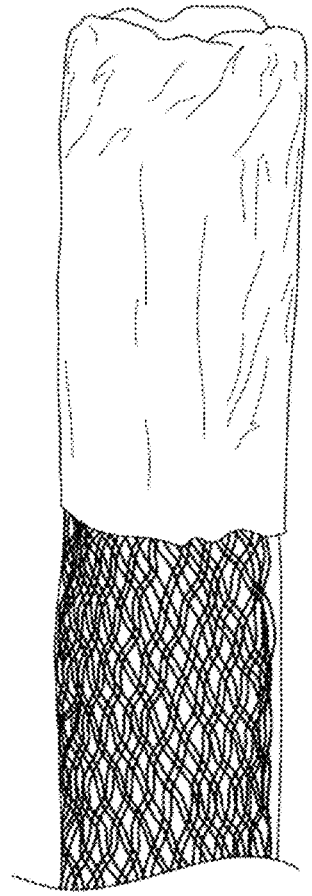

FIG. 13B is a side view of a prototype of the inversion support catheter of FIG. 13A shown in a side perspective view in a collapsed (non-expanded) configuration. FIG. 13C shows the funnel in the expanded configuration. The Teflon sleeve 1309 is shown attached on the outside of the expanded funnel, partially down the length of the funnel. FIG. 13D shows an end view of the distal end of the funnel of the inversion support catheter of FIGS. 13B-13C.

FIGS. 14A-14C illustrate different examples of lubricious sleeves that may be included with any of the apparatuses shown. In FIG. 14A a Teflon sleeve (PTFE tube) is attached within the mouth of the funnel and mat be attached at the distal end but allowed to float at the proximal end. Alternatively in FIG. 14B, the lubricous sleeve (PTFE sleeve) is attached under the woven body forming the funnel shape, and may be bonded at the proximal end or allowed to float. In FIG. 14C the lubricous sleeve is attached on the outside and inverts over the distal end of the funnel shape, and is allowed to float proximally (or may be attached proximally).

Figure 15B:
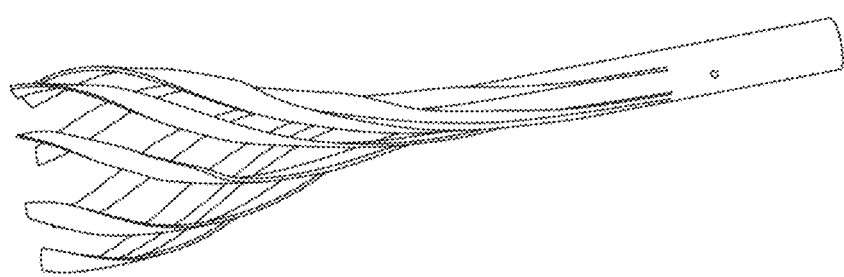
FIG. 15B is an example of a frame cut to form a funnel at the distal end of an inversion support catheter, having curved struts (fingers) forming the funnel region.
Figure 15A:
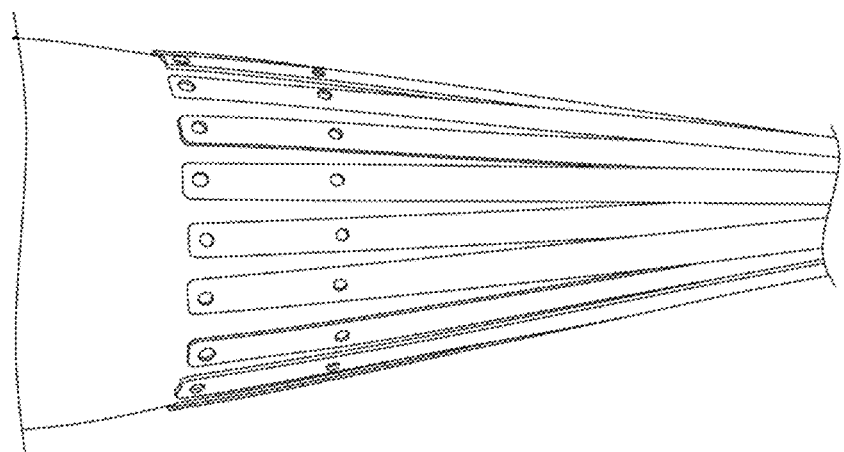
FIG. 15A is an example of a frame cut to form a funnel at the distal end of an inversion support catheter.

FIGS. 15A and 15B illustrate other variation of inversions support catheters including funnels. In FIG. 15A, the funnel is formed of a set of laser-cut fingers cut and formed into a funnel; a funnel body material may be attached within the inside of the funnel shape and/or over these shapes, as described above. In FIG. 15B the end of the catheter body may be laser cut into a plurality of curving arms that may form a funnel-shape.

Figure 16B:
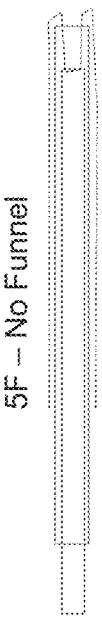
FIGS. 16A-16D illustrate examples of thrombectomy devices having different sizes that may be selected by a user based on the vessel and/or clot size.
Figure 16A:
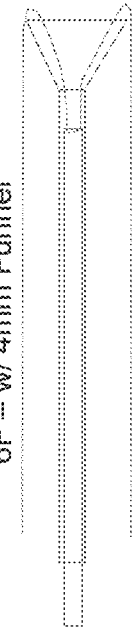
Figure 16C:
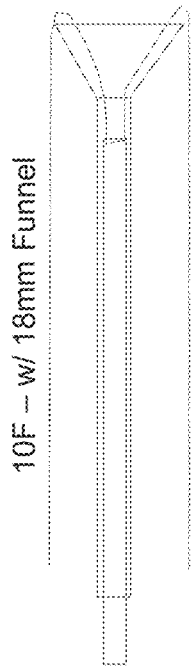
Figure 16D:
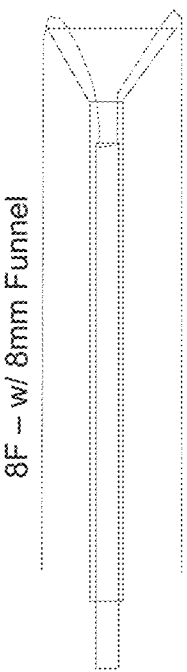

As mentioned, a variety of different configurations and sizes may be used, and a user may select between them based on the dimensions of the vessel into which the apparatus is to be used. For example, FIGS. 16A-16D show four variations of inverting tube apparatuses that may be used. In FIG. 16A, a 5 French apparatus is shown, which does not include a funnel on the distal end of the inversion support catheter. FIG. 16B show an example (sized for a 6F system) that does include an inversion support catheter having an expandable funnel. FIGS. 16C and 16D illustrate 8F and 10F apparatuses, respectively.

Figure 17A:
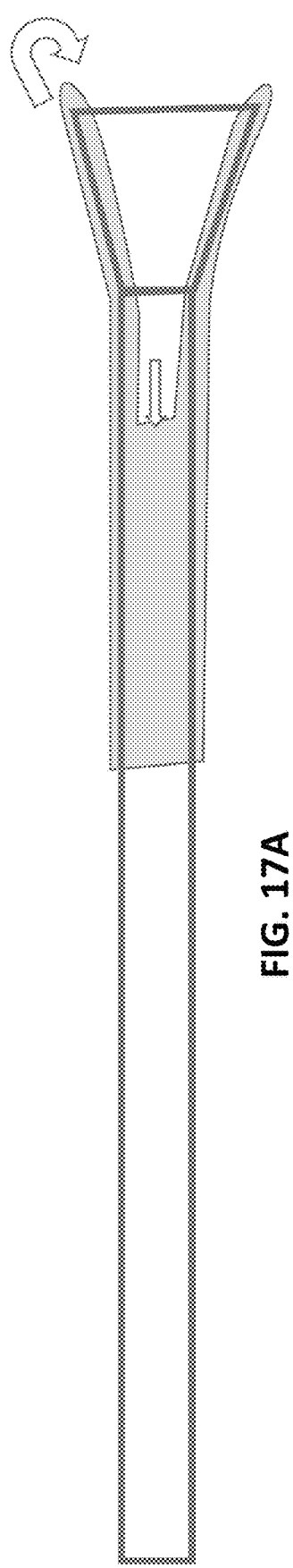
FIGS. 17A-17C illustrate example of inverting tube apparatuses that may be used for removing an atheroma (e.g., atherectomy)
Figure 17B:
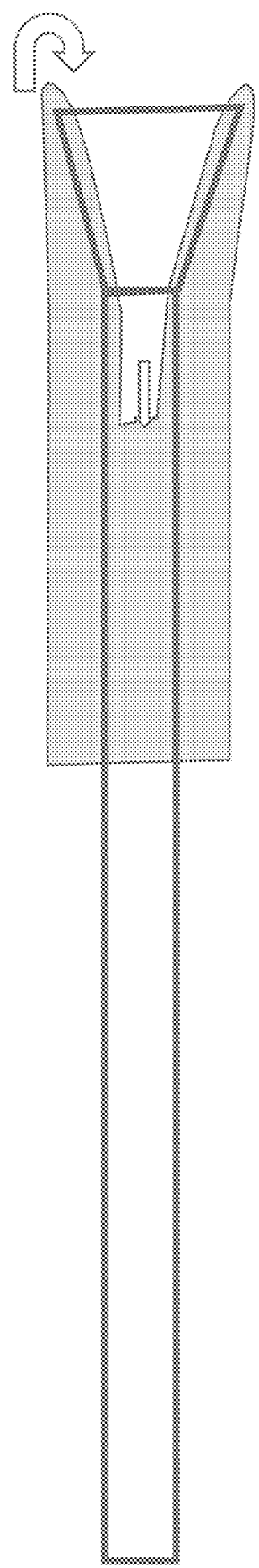
Figure 17C:
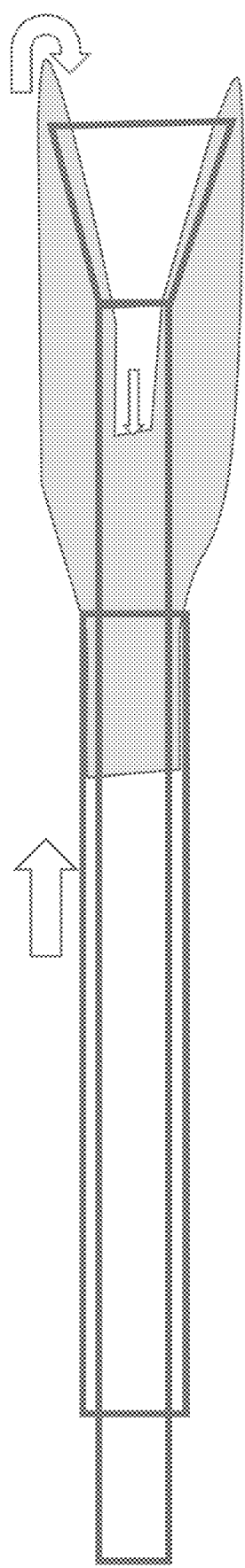

FIGS. 17A-17C illustrate variations in which the flexible tube is configured to have an expanded (e.g. non-compressed) configuration that is narrow (FIG. 17A), e.g., less than the maximum OD of the expanded funnel, or broad (FIGS. 17B and 17C), e.g., larger than the maximum OD of the expanded funnel. In FIG. 17C the delivery catheter 1705 may be used to drive the flexible tube distally (e.g., to prevent tension) when rolling the flexible tube over the funnel at the distal end of the inversion support catheter by pulling the first end of the flexible tube proximally within the inversion support catheter.

Figure 18A:
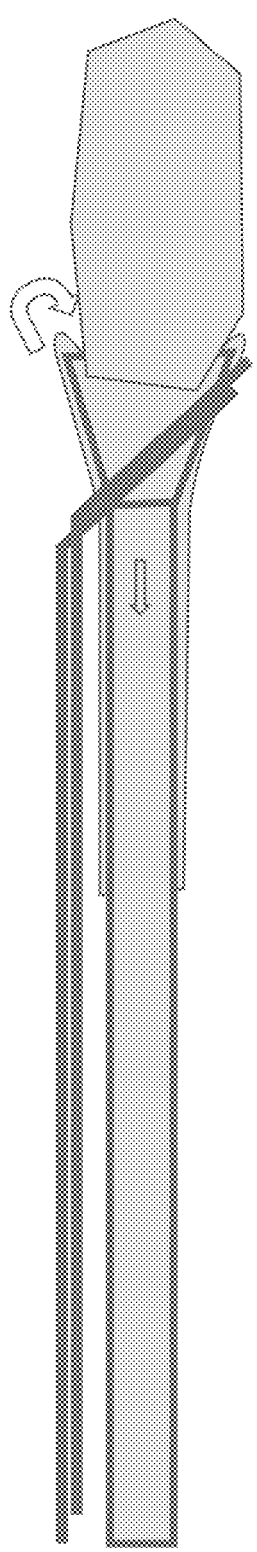
FIGS. 18A-18C illustrate one method of removing an atheroma using an inverting tube apparatus and a pair of cutting rings.
Figure 18B:
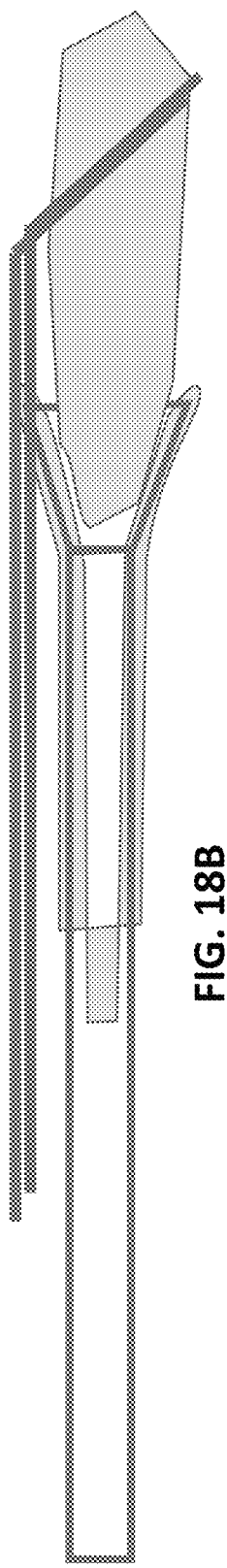
Figure 18C:
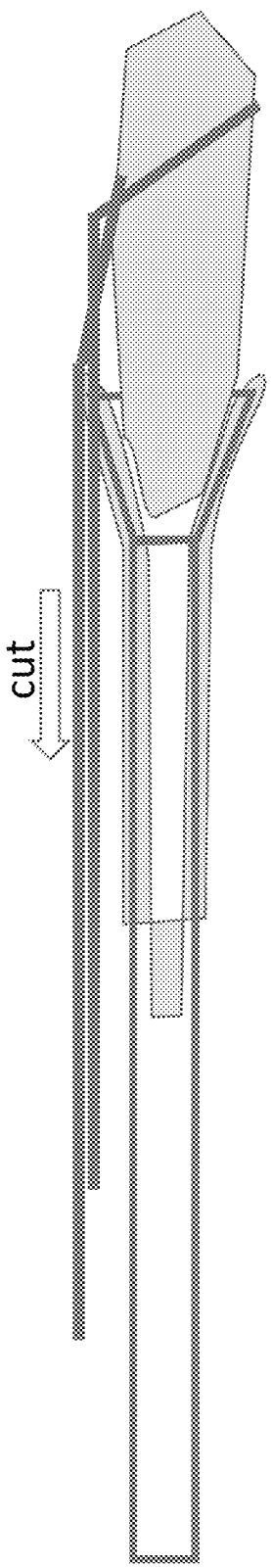

Also described herein are inverting tube apparatuses configured for atherectomy. In some variations the inverting tube apparatus includes the flexible tube and inversion support catheter (e.g., with an expandable funnel at the distal end) and may also include one or more ring cutters for cutting into and/or around atheroma within a vessel. For example, FIG. 18A illustrates an example of an inverting tube apparatus including a pair of ring cutters (e.g., a MollRing Cutter) that may be used to cut laterally through an atheroma. The ring cutters may pass over the outside of the inversion support catheter. The rolling, inverting flexible tube in some variations may be formed of a sharp or cutting material, such as a sheet of laser-cut material (e.g., metal, polymeric, etc.) that is cut at an angle relative to the perpendicular, so as to have a sharp edge that may engage and cut calcified material and/or tissue. The cutting rings may further allow cutting into and through a dense plaque material.

Figure 25:
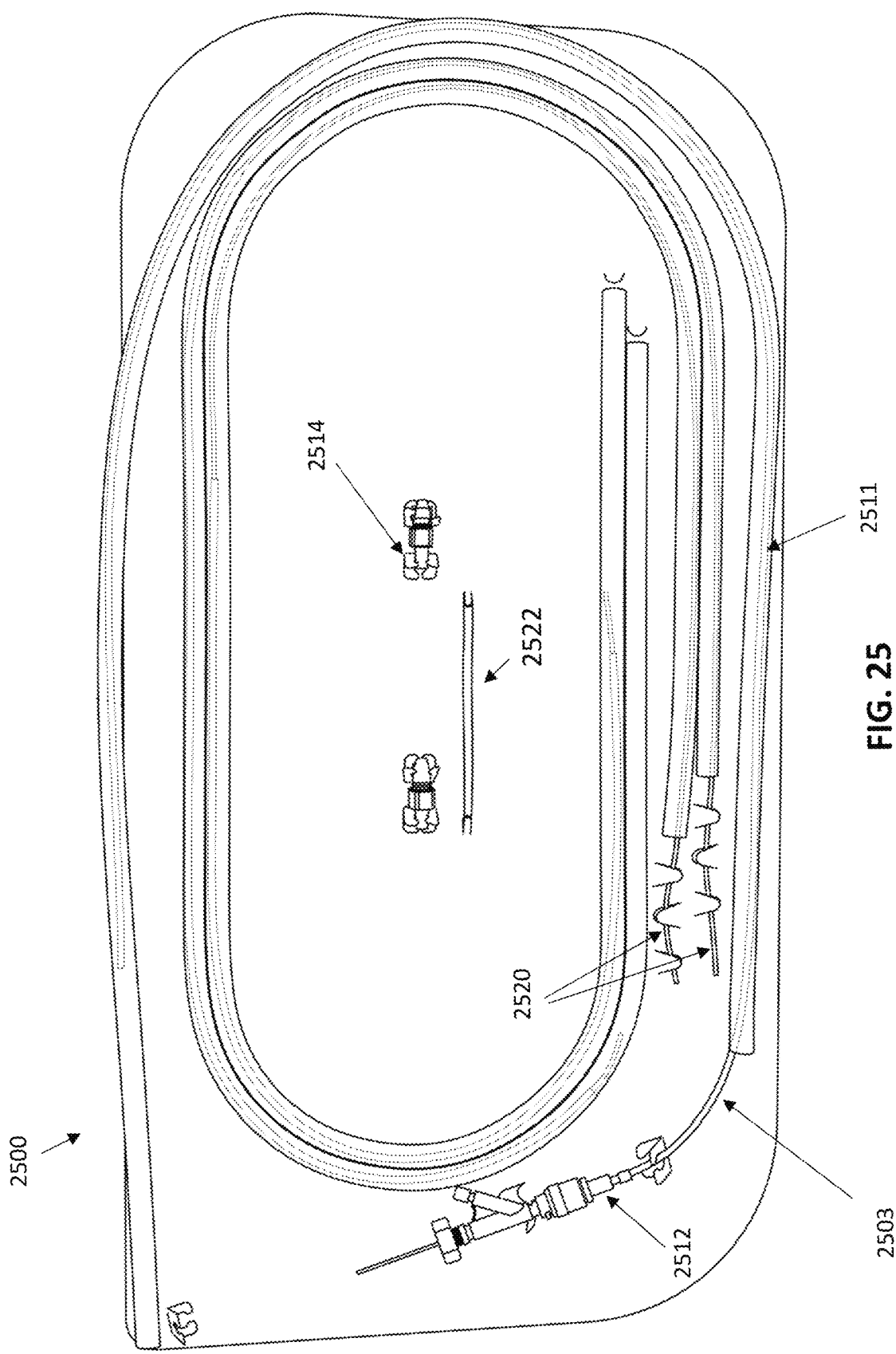
FIG. 25 is an example of a system including an inversion support catheter having an elongate and flexible body and an expandable funnel, with a flexible tube of knitted material extending distally along an outer surface of the inversion support catheter, a loading sleeve and a tear-away sleeve extending over the flexible tube and the inversion support catheter, as well as a pair of locks configured to lock the inversion support catheter to a delivery catheter (not shown) and a second flexible tube of knitted or woven material configured to be inserted into the inversion support catheter.

Any of the inversion support catheters described herein that include an expandable/collapsible funnel at their distal end may be configured to collapse to a small diameter for easy insertion into a catheter and/or sheath, including when a flexible tube (e.g., tractor) is preloaded around the funnel. In use, a tool, such as an introducer sheath may be used to hold the distal end (e.g., the funnel) of the inversion support catheter, with or without a flexible tube attached, in a collapsed form so that it may be easily inserted into a lumen of a delivery catheter that may already be positioned within the body or that may be loaded into the body with the inversion support catheter and flexible tube assembly inserted. Collapsing the funnel at the distal end into a smaller diameter may help thread the "loaded" inversion support catheter into the delivery catheter and therefore into the body. If a tool such as an introducer sheath is used, it may be removed during or after loading; the introducer sheath may be a polymeric (e.g., plastic) tapered tube with a slit, perforation or tear-away region extending along the length. The funnel may be collapsed and inserted into the wider end of the introducer sheath and the inversion support catheter may be pushed to slide distally within the introducer sheath towards the narrower end. The narrow end may then be loaded into the delivery catheter and the inversion support catheter may be pushed distally out of the introducer sheath and into the delivery catheter; the introducer sheath may then be torn down its length (e.g., along the pre-formed tear line) to remove it from around the inversion support catheter. An example of an introducer sheath is shown in FIG. 25, described in greater detail below.

The funnel portion of an inversion support catheter may be configured to collapse, at least the distal end region, down to less than the diameter of the rest of the inversion support catheter, e.g., the region proximal to the funnel. For example, the funnel may be configured to collapse down to fit into a 3F, 4F, 5F, 6F, 7F, 8F, 9F, 10F, 12F, 14F, 16F, 18F, 20F, 24F, 30F, etc. sheath or guide catheter (also referred to herein as a delivery catheter).

The funnel portion of the inversion support catheter may be adapted for this purpose in a variety of ways, including, but not limited to, the features of the components forming the funnel portion. For example, in some variations the outer and inner surfaces of the funnel portion may be formed of a mesh material, such as a braid. The specific mesh or braid structure may contribute to the amount that the funnel can collapse, such as the number of number of filaments forming the braid (e.g., the number of ends), the size of the filaments (e.g., the size of ends), the braid angle, etc. In some variations in which the funnel includes a plurality of longitudinal tines between an inner and outer surface formed by the mesh or other material, the ability of the funnel portion to collapse may be determined in part by the ability of the tines to move within the inner and outer surfaces (e.g., of the mesh or woven material forming the walls of the funnel). For example a braided tube forming the funnel wall may slide relative to the tines to allow the funnel to collapse to small diameter for introduction.

FIG. 19 shows a portion of one example of an inversion support catheter having a funnel at the distal end. The funnel may be formed in part by a plurality of tines 1905 extending from the distal end of the inversion support catheter. For example, the distal end region of the inversion support catheter may be formed of a metallic hypotube that is cut, e.g., by laser cutting laterally, to form tines. In FIG. 19, six tines are shown. The tines may be flared outward from each other, e.g., on a mandrel (as shown in FIG. 20A). In some variations the tines may be formed by folding the cut 'arms' back on themselves so that the distal ends 1909 are blunted or rounded, as shown in FIG. 19. In this example, the folded over portion of the tine 1907 may be folded inward and crimped together, as shown. In some variations a filament may be included to radially connect each tine of the plurality of tines. This is illustrated in FIGS. 20A and 20B. In this example the filament 2007 is a suture that is threaded at the distal ends of the tines 2005 (where they are folded back on themselves). Typically the filament is attached at or near the distal end (e.g., within 1 mm, 2 mm, 3 mm, 4 mm, etc. from the distal end) of the tines. Each of the tines 2005 shown is connected to a radially adjacent tine by a filament 2007. Connecting the tines to each other along their length, including at their distal ends, may help distribute the forces that may otherwise cause a tine to collapse and/or bend, impairing the function of the inversion support catheter.

Figure 21A:
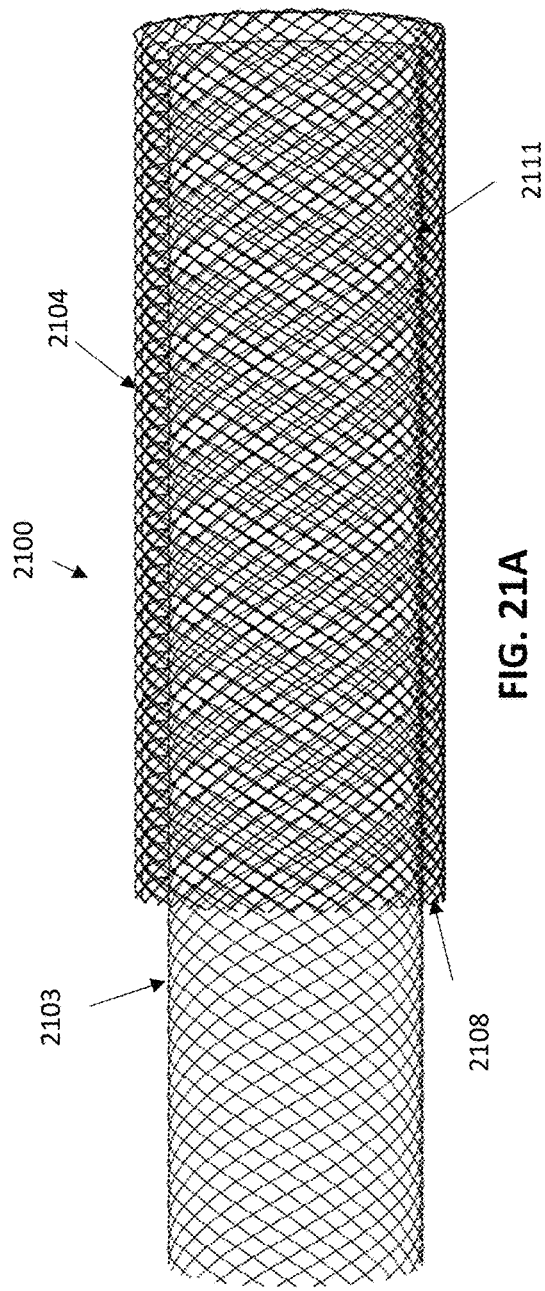
FIG. 21A is an example of a flexible tube of woven material that may form the funnel surface of an expandable funnel of an inversion support catheter; the woven material is inverted over itself and shape (e.g., heat) set so that there is a space between the outer funnel surface and the inner funnel surface in which tines may fit.
Figure 21B:
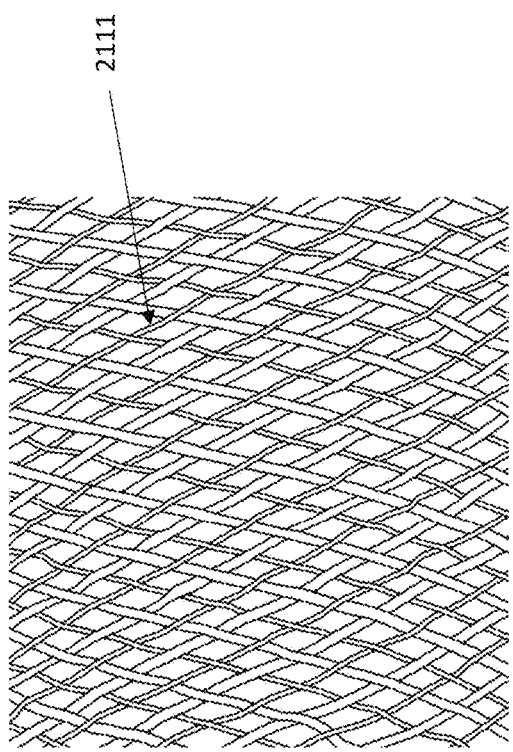
FIG. 21B shows an enlarged view of the flexible tube of FIG. 21A.

FIGS. 21A and 21B illustrate an example of a mesh material that may be used to form the outer and inner surfaces (e.g., the wall) of the funnel. A tube of mesh (e.g., woven) material 2100 is shown in FIG. 21A, which has been inverted back over itself as shown, forming an inner surface 2103 and an outer surface 2104. To form the funnel, the tines may be inserted into the space 2108 between these inner and outer surfaces and the outer end may be attached to the outside of the proximal region of the inversion support catheter. The material (e.g., braid) forming the walls may be shape set (e.g., heat set) into this double layer. In particular, the material may be shape set so that, in the jammed configuration, the inner layer has a smaller outer diameter (OD) than the outer layer's inner diameter (ID), which may create a space for the tines to slide.

FIG. 21 B shows an enlarged view of a portion of the braided wall material of FIG. 21A. In FIG. 21B, the braided material is shown as braids of flat wire 2111; round and/or flat cross-sectional wire may be used to form the braided material. As described above, the braid angle may be selected to allow compression of the funnel as well as setting the jamming configuration, at which the funnel is maximally expanded.

FIGS. 22A-22C illustrate a funnel 2200 formed by applying the braded wall material, such as shown in FIG. 21A onto the tines at the distal end of the inversion support catheter, such as shown in the example of FIG. 19. In FIG. 22A the inner and outer walls of the woven material forming the funnel are stitched together by a suture 2221 that is arranged radially around the funnel and may constrain it from expanding further, as described above. The tines may slide axially relative to the inner and outer walls. In any of the funnels described herein the mesh material forming the inner and outer walls may extend distally further than the distal end of the tines. In the relaxed configuration, shown in FIG. 22A, the braid length distal to the distal ends of the tines 2214 is shown as a distance $x_1$ mm. FIG. 22B shows the funnel with the braid jammed 2213, as it would be if the tractor (e.g., the flexible tube) were loaded over the funnel and pulled proximally into the inversion support catheter. In this configuration the axial length of the braided wall extending beyond the tip of the tines as $x_2$ mm. FIG. 22C shows the collapsed (and loaded into an introducer sheath 2217) so that the axial length of the braided wall extending beyond the tip of the tines is $x_3$ mm.

In some variations it may be beneficial to limit the axial length of the braided wall extending beyond the tip of the tines in the fully expanded (e.g., jammed) configuration. This may prevent instability, and particularly lateral instability. For example, it may be beneficial to limit the axial length of the braided wall extending beyond the tip of the tines in the fully expanded (e.g., jammed) configuration to 10 mm or less (e.g., 8 mm or less, 7 mm or less, 6 mm or less, 5 mm or less, 4 mm or less, 3 mm or less, 2 mm or less, such as between 1 mm and 10 mm, between 1 mm and 8 mm, between 1 mm and 7 mm, between 1 mm and 6 mm, between 1 mm and 5 mm, between 1 mm and 4 mm, etc.). In particular, it may be beneficial to limit it to 5 mm or less.

Figure 23:
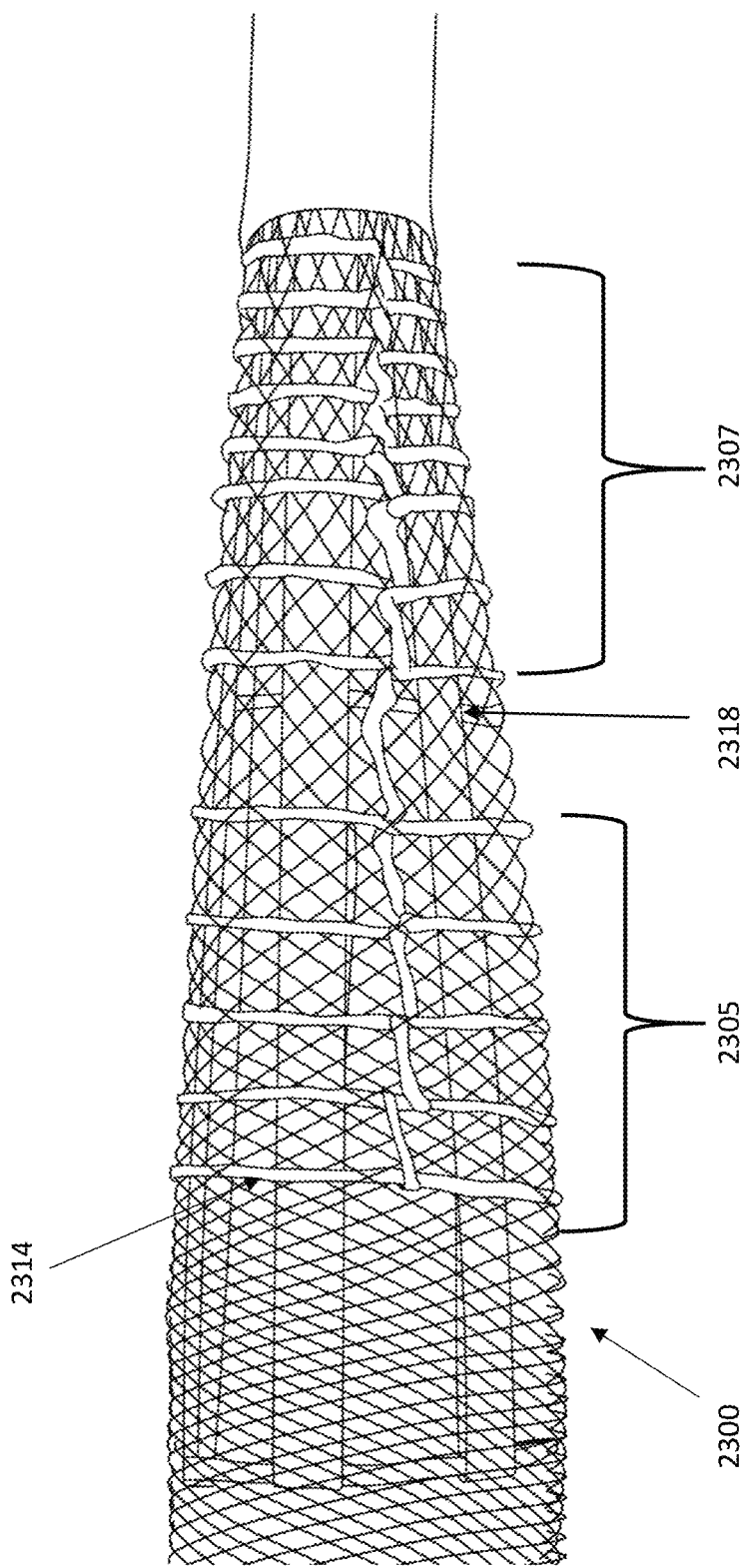
FIG. 23 is another example of an expandable funnel of an inversion support catheter.

FIG. 23 shows another example of an inversion catheter including a funnel as described above. In this example, the funnel 2300 includes a suture 2314 (e.g., a restraining filament) integrated between inner and outer layers (e.g., walls) of funnel to prevent relative sliding of the inner and outer braid layer, so the braid jams at the tip, while allowing sliding of the tines 2318 between the inner and outer braided material walls. The suture limits the diameter 2305, 2307 of the funnel in the expanded configurations, as shown.

In some variations, the outer diameter of the funnel at various positions along the length of the funnel may be limited or set by the use of a restraining filament, such as a suture, wire, etc. The restraining filament(s) may be referred to herein as circumferential supports extending radially around the funnel surface and constraining the maximum outer diameter of the expandable funnel. The restraining filament may be held in place by stitching it into the mesh (e.g., woven) material forming the funnel wall(s). Thus, the filament may constrain the OD of the funnel to a desired diameter/profile.

As discussed above, each of these funnels includes a porous structure to enable clot or tissue to be partially desiccated when pulled into through base of funnel, by allowing fluids to ooze out through the side of the funnel. The funnels described herein may have a smooth transition from the funnel ID to the catheter ID. This may be achieved by laser cutting the tines at the distal of the catheter, as shown. The porous structure and/or the smooth transition may also be provided in these examples by the porous metallic mesh (e.g., braid) structure forming the walls.

The inversion support catheters described and illustrated herein may be adapted to prevent collapse, even when force is applied by the flexible tube either without or with a clot material. In any of these variations, the funnel needs to be able to handle axial loads (e.g., loads applied along axis of catheter shaft length) that may be in excess of 1, 2, 3, 4, 5, 10, 15 and/or 20 kg, without collapsing, e.g., when there is resistance ingesting the clot, while still allowing the flexible tube (e.g., tractor) to roll around the top of the funnel and into the inversion support catheter. Axial stiffness may be achieved at least in part by configuring the braided wall of the funnel have a jammed configuration at tip as described above. Axial stiffness may also be improved by limiting the length of the braided wall extending beyond the distal tips of the tines in the jammed configuration (e.g., to 5 mm or less). In some configuration, axial stiffness may also be improved by including the circumferential support (e.g., filament) between the tines, as described above, which may distribute the load exerted from the tractor on the funnel tip, so that the funnel tips stays round and no one finger gets isolated and collapses.

In general, these same factors may improve the radial stiffness as well. The end of the funnel may also preferably be sufficiently stiff to prevent the funnel from collapsing radially when the tractor rolls around the tip. Radial stiffness of funnel may be achieved at least in part by configuring the braided wall of the funnel have a jammed configuration at tip as described above. Radial stiffness may also be improved by limiting the length of the braided wall extending beyond the distal tips of the tines in the jammed configuration (e.g., to 5 mm or less). In some configuration, radial stiffness may also be improved by including the circumferential support (e.g., filament) between the tines, as described above, which may distribute the load exerted from the tractor on the funnel tip, so that the funnel tips stays round and no one finger gets isolated and collapses.

In any of the funnels described herein, the funnel may be configured so that it only fully expands when the axial loads are applied, e.g., when pulling the flexible tube (e.g., tractor) proximally to roll into the inversion support catheter. This may allow the funnel to be advanced in smaller vessels before it is actuated.

Figure 24:
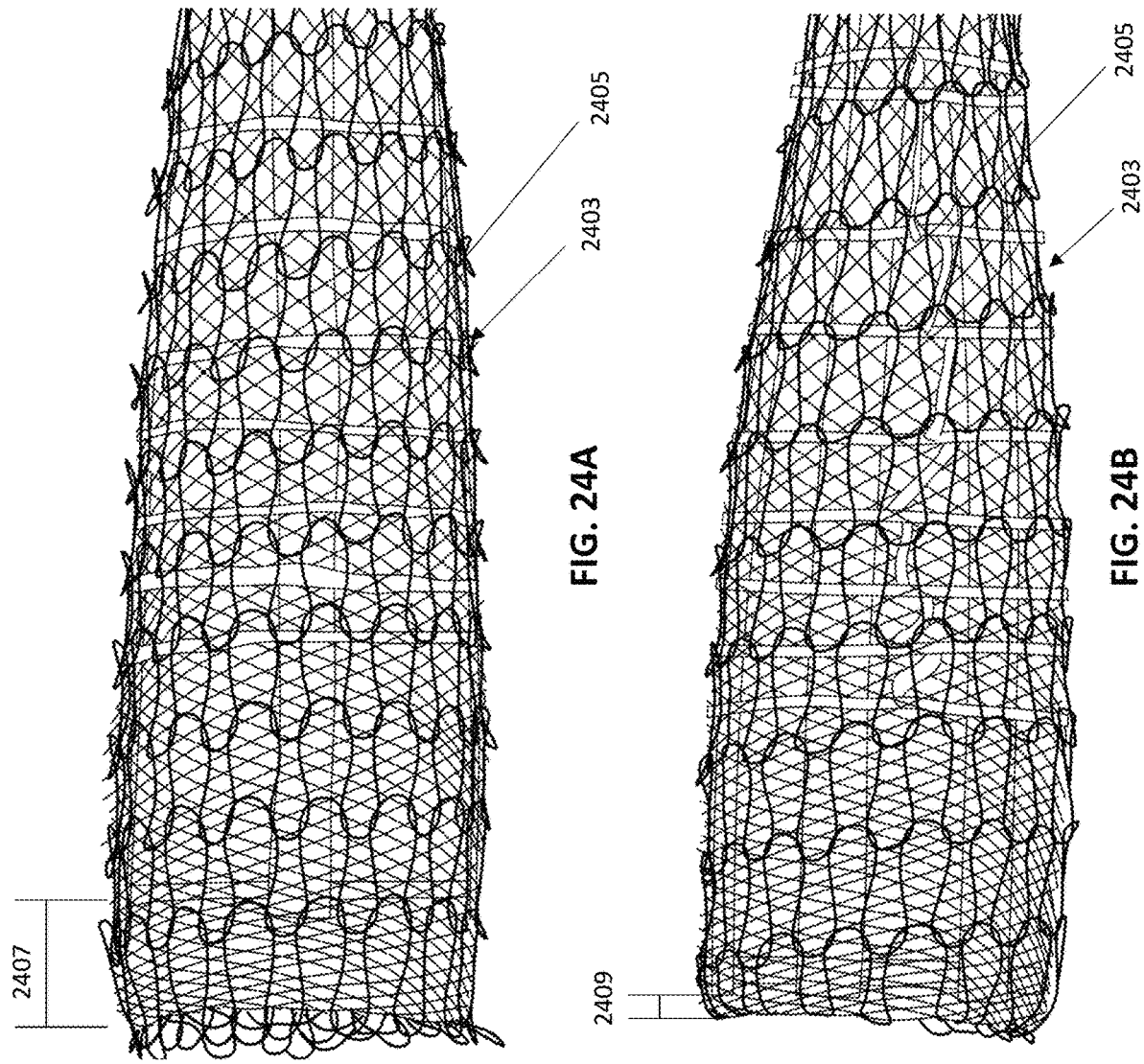
FIG. 24A shows an example of an expandable funnel of an inversion support catheter with a flexible tube of knitted material extending distally along an outer surface of the inversion support catheter and inverting into the inversion support catheter.
FIG. 24B shows the system of FIG. 24A when tension is applied to pull the tube of knitted or woven material into the inversion support catheter, fully expanding and jamming the funnel body in the expanded configuration, as shown.

For example, FIG. 24A illustrates on example of an assembly including an inversion support catheter having a funnel as described above, with a flexible tube loaded onto and into the inversion support catheter so that the flexible tube (tractor) extends along the outside of the inversion support catheter and over the funnel before inverting into the interior of the funnel, as shown. In FIG. 24A, the funnel 2405 is not fully expanded and the knit flexible tube 2403 is not being drawn into the inversion support catheter. In FIG. 24B the flexible tube 2403 is pulled into the inversion support catheter so that it rolls into the catheter; in doing so, the flexible tube/tractor applies axial load and fully extends the funnel 2405 to a jammed configuration. The portion of the funnel wall extending beyond the tines 2407 in the relaxed configuration shown in FIG. 24A is greater than the length of the funnel wall extending beyond the tines 2409 in the jammed configuration shown in FIG. 24B.

As mentioned above, any of the apparatuses described herein may be packaged or otherwise included together to form a kit, e.g., for removing a thrombus. For example, FIG. 25 shows one illustration of a systems for performing a thrombectomy that is packaged together. In FIG. 25, the system 2500, includes pre-loaded component such as an inversion support catheter 2512 that has been pre-loaded with a tractor (flexible tube); the assembly of the flexible tube and inversion support catheter is shown enclosed in a loading sheath 2503 (a spare loading sheath 2522 is also shown) for loading into a delivery catheter (not shown). The assembly of the flexible tube and inversion support catheter is also proximally covered in a tear-away sleeve 2511 extending over the flexible tube and the inversion support catheter and configured to be removed from over the flexible tube by tearing along a length of the tear-away sleeve as the inversion support catheter and flexible tube are loaded into a delivery catheter. A pair of locks 2514 are also shown as part of the kit in FIG. 25. In FIG. 25 a pair of additional tractors 2520 (flexible tubes) connected to a puller are also included. These additional flexible tubes may be loaded into the inversion support catheter after completely removing the pre-loaded tractor.

For example, an additional flexible tube may be loaded onto an inversion support catheter after the original inversion support catheter has been pulled through the lumen of the inversion support catheter, e.g., when removing a clot. In some variations the additional flexible tube may be attached to a puller and the puller and a portion of the additional flexible tube (e.g., the first portion) may be pulled through the distal end (funnel end) of the inversion support catheter while the second portion may be pulled over the outside of the inversion support catheter.

Any of the inversion support catheters 2601 described herein may include a stop 2607, as shown in FIG. 26. The stop may prevent the proximal end of the tractor (flexible tube) 2603 from pushing proximally past the stop, e.g., when loading the assembly of the flexible tube and inversion support catheter into the delivery catheter, as described above, and/or when loading a flexible tube onto the inversion support catheter. For example, the stop may engage with a cuff (e.g., an elastic cuff) 2609 on the end of the tractor. The tear-away sleeve may also help reduce or prevent this.

FIGS. 27A and 27B illustrate an example of a lock 2701 that may be used to secure an inversion support catheter 2711 to a delivery catheter 2713 so that the two portions may be moved together. As shown in FIG. 27A, the lock may include an annular clamp 2703 for connecting to the outside of the inversion support catheter, as well as an L- or J-shaped lock 2705 for coupling to the end of the delivery catheter. By loosening or tightening the annular clamp, the inversion support catheter may be permitted to slide separately or coupled together with the delivery catheter.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A thrombectomy system, comprising:
an inversion support catheter having an elongate and flexible catheter body, a catheter lumen, and an expandable funnel disposed at a distal end of the catheter body, wherein a distal end of the funnel defines a distal opening in communication with an interior of the funnel and the catheter lumen, respectively; and
a flexible tube inverting over the distal end of the funnel such that the flexible tube has a first region at least partially disposed within the interior of the funnel and a second region at least partially extending over an exterior of the funnel, wherein the flexible tube is configured to be pulled proximally into the catheter lumen by pulling the first region proximally so that the second region rolls over the distal end of the funnel as the flexible tube is pulled into the catheter lumen.

2. The system of claim 1, wherein a portion of the second region of the flexible tube extends at least partially over an outer surface the catheter body proximal of the funnel, and wherein an inner diameter of the portion of the second region extending over the outer surface of the catheter body is less than a maximum outer diameter of the funnel when the funnel is in an expanded configuration.

3. The system of claim 1, wherein a base region of the funnel adjacent to the distal end of the catheter body comprises openings configured to allow fluid to pass therethrough.

4. The system of claim 1, wherein the funnel comprises a circumferential porous region at a base of the funnel adjacent to the distal end of the catheter body, the porous region configured to allow fluid to pass therethrough.

5. The system of claim 1, wherein the funnel has a collapsed configuration having a maximum outer diameter of less than 0.3× an outer diameter of the catheter body proximal of the funnel.

6. The system of claim 1, wherein the funnel has an expanded configuration in which the funnel has a minimum outer diameter of greater than 2× an outer diameter of the catheter body proximal of the funnel.

7. The system of claim 6, wherein the funnel has an outer diameter of between 2 and 26 mm in the expanded configuration.

8. The system of claim 1, wherein the flexible tube comprises a knitted tube.

9. The system of claim 8, wherein the knitted tube has greater than 10 loops per transverse section through the knitted tube along a length of the knitted tube.

10. The system of claim 1, wherein the funnel is configured assume a jammed configuration when the first region of the flexible tube is pulled proximally and exerts an axial compressive force on the distal end of the funnel.

11. The system of claim 10, wherein in the jammed configuration, the funnel has a greater column strength than when the funnel is not in the jammed configuration.

12. The system of claim 10, wherein in the jammed configuration, the funnel is configured to withstand greater than 1200 g of compressive force without collapsing.

13. The system of claim 12, wherein the funnel comprises a plurality of longitudinal tines that are continuous with the catheter body proximal of the funnel.

14. The system of claim 13, wherein the funnel further comprises a mesh inverted over itself at the distal end of the funnel such that a first portion of the mesh forms an inner funnel surface and a second portion of the mesh forms an outer funnel surface, and wherein the plurality of longitudinal tines are positioned between the inner funnel surface and the outer funnel surface.

15. The system of claim 1, further comprising a lubricious sleeve disposed over at least a portion of the funnel.

16. The system of claim 1, further comprising an intermediate catheter, wherein the inversion support catheter is at least partially slidably disposed in a lumen of the intermediate catheter.

17. The system of claim 16, further comprising a puller disposed within the catheter lumen, wherein the first region of the flexible tube is coupled to a distal end region of the puller.

18. A thrombectomy system, comprising:
an inversion support catheter having an elongate and flexible catheter body, a catheter lumen, and an expandable funnel disposed at a distal end of the catheter body, wherein a distal end of the funnel defines a distal opening in communication with an interior of the funnel and the catheter lumen, respectively, and wherein at least a proximal portion of the funnel adjacent to the catheter body comprises openings configured to allow fluid to pass therethrough;
a puller disposed within the catheter lumen; and
a flexible tube formed of a knitted or woven material, the flexible tube inverting over the distal end of the funnel and having a first region attached to the puller and a second region at least partially extending over an exterior surface of the funnel, wherein the flexible tube is configured to be pulled proximally into the catheter lumen by pulling the puller proximally so that the second region of the flexible tube passes through the funnel interior and into the catheter lumen, respectively.

19. A thrombectomy system, comprising:
an inversion support catheter having an elongate and flexible catheter body, a catheter lumen, and an expandable funnel disposed at a distal end of the catheter body, wherein a distal end of the funnel defines a distal opening in communication with an interior of the funnel and the catheter lumen, respectively, and wherein at least a proximal end of the funnel adjacent to the catheter body comprises openings configured to allow fluid to pass therethrough; and
a flexible tube that is knitted, the flexible tube inverting over the distal end of the funnel and having a first region at least partially disposed within the interior of the funnel and a second region at least partially extending over an exterior of the funnel, wherein the flexible tube is configured to be pulled proximally into the catheter lumen by pulling the first region of the flexible tube proximally so that the second region of the flexible tube rolls over the distal end of the funnel as it is pulled into the funnel interior and catheter lumen, respectively, and wherein the funnel is configured such that pulling the first region of the flexible tube proximally applies an axial load on the funnel that expands the funnel into an expanded and jammed configuration.

* * * * *